(12) United States Patent
Solorzano et al.

(10) Patent No.: US 10,512,552 B2
(45) Date of Patent: Dec. 24, 2019

(54) METHODS, DEVICES, AND SYSTEMS FOR THE FABRICATION OF MATERIALS AND TISSUES UTILIZING ELECTROMAGNETIC RADIATION

(71) Applicant: BIOBOTS, INC., Philadelphia, PA (US)

(72) Inventors: Ricardo D. Solorzano, Garnet Valley, PA (US); Sohaib K. Hashmi, Philadelphia, PA (US); Daniel Cabrera, San Francisco, CA (US)

(73) Assignee: BIOBOTS, INC., Philadelphia, PA (US)

( * ) Notice: Subject to any disclaimer, the term of this patent is extended or adjusted under 35 U.S.C. 154(b) by 145 days.

(21) Appl. No.: 15/128,632

(22) PCT Filed: Mar. 25, 2015

(86) PCT No.: PCT/US2015/022458
§ 371 (c)(1),
(2) Date: Sep. 23, 2016

(87) PCT Pub. No.: WO2015/148646
PCT Pub. Date: Oct. 1, 2015

(65) Prior Publication Data
US 2017/0172765 A1    Jun. 22, 2017

Related U.S. Application Data

(60) Provisional application No. 62/046,279, filed on Sep. 5, 2014, provisional application No. 61/969,832, filed on Mar. 25, 2014.

(51) Int. Cl.
*B29C 67/00*    (2017.01)
*A61F 2/50*     (2006.01)
(Continued)

(52) U.S. Cl.
CPC ............ *A61F 2/5044* (2013.01); *A61L 27/26* (2013.01); *A61L 27/3834* (2013.01);
(Continued)

(58) Field of Classification Search
CPC ............ A61F 2/5044; A61F 2002/505; C12N 5/0662; C12N 2513/00; C12N 2533/30;
(Continued)

(56) References Cited

U.S. PATENT DOCUMENTS

D446,826 S    8/2001  Dunn et al.
D514,556 S    2/2006  Rising
(Continued)

FOREIGN PATENT DOCUMENTS

GB    2478801 A       9/2011
WO    WO-2006-020685 A2    2/2006
(Continued)

OTHER PUBLICATIONS

Fairbanks, B.D. et al, "Photoinitiated polymerization of PEG-diacrylate with lithium phenryl-2,4,6-trimethylbenzoylphosphinate: polymerization rate and cytocompatibility", Biomaterials, Dec. 2009, 30(35): 6702-6707.
(Continued)

*Primary Examiner* — Nahida Sultana
(74) *Attorney, Agent, or Firm* — DLA Piper, LLP (US)

(57) ABSTRACT

The present invention provides a three-dimensional bioprinter for fabricating cellular constructs such as tissues and organs using electromagnetic radiation (EMR) at or above 405 nm. The bioprinter includes a material deposition device comprising a cartridge for receiving and holding a composition which contains biomaterial that cures after exposure to EMR. The bioprinter also includes an EMR module that emits EMR at a wavelength of about 405 nm or higher. Also provided is a bioprinter cartridge which contains cells and a
(Continued)

material curable at a wavelength of about 405 nm or greater. The cells are present in a chamber and are extruded through an orifice to form the cellular construct.

26 Claims, 23 Drawing Sheets

(51) Int. Cl.

| | |
|---|---|
| *A61L 27/26* | (2006.01) |
| *C12M 3/00* | (2006.01) |
| *B41J 2/04* | (2006.01) |
| *C12M 1/26* | (2006.01) |
| *B33Y 80/00* | (2015.01) |
| *B33Y 70/00* | (2015.01) |
| *B29C 64/112* | (2017.01) |
| *B29C 64/20* | (2017.01) |
| *A61L 27/38* | (2006.01) |
| *C12N 5/00* | (2006.01) |
| *C12N 5/0775* | (2010.01) |
| *B29L 31/00* | (2006.01) |
| *B29K 71/00* | (2006.01) |

(52) U.S. Cl.
CPC .......... *B29C 64/112* (2017.08); *B29C 64/20* (2017.08); *B33Y 70/00* (2014.12); *B33Y 80/00* (2014.12); *B41J 2/04* (2013.01); *C12M 21/08* (2013.01); *C12M 33/00* (2013.01); *C12M 33/04* (2013.01); *C12N 5/0062* (2013.01); *C12N 5/0662* (2013.01); *A61F 2002/505* (2013.01); *A61L 2430/14* (2013.01); *B29K 2071/02* (2013.01); *B29K 2995/0056* (2013.01); *B29L 2031/7532* (2013.01); *B41J 2002/041* (2013.01); *C12N 2513/00* (2013.01); *C12N 2533/30* (2013.01)

(58) Field of Classification Search
CPC ... C12N 5/0062; A61L 27/3834; A61L 27/26; A61L 2430/14; B29C 64/112; B29C 64/20; C12M 33/04; C12M 21/08; C12M 33/00; B33Y 70/00; B33Y 80/00; B41J 2/04; B41J 2002/041; B29K 2995/0056; B29K 2071/02; B29L 2031/7532
See application file for complete search history.

(56) References Cited

U.S. PATENT DOCUMENTS

| | | | |
|---|---|---|---|
| 7,297,304 B2 | 11/2007 | Swanson et al. | |
| D616,045 S | 5/2010 | Tervo | |
| D677,723 S | 3/2013 | Buel et al. | |
| D681,548 S | 5/2013 | Zhang et al. | |
| D688,741 S | 8/2013 | Joyce | |
| D698,869 S | 2/2014 | Strzelewicz et al. | |
| D711,463 S | 8/2014 | Costabeber | |
| 9,039,998 B2 | 5/2015 | Guillemot et al. | |
| D730,979 S | 6/2015 | Anantha et al. | |
| D732,586 S | 6/2015 | Chen et al. | |
| D732,587 S | 6/2015 | Hsu et al. | |
| D732,588 S | 6/2015 | Lin et al. | |
| D733,196 S | 6/2015 | Wolf et al. | |
| D734,788 S | 7/2015 | Reches et al. | |
| D734,814 S | 7/2015 | Yeh et al. | |
| D737,345 S | 8/2015 | Anantha et al. | |
| D737,346 S | 8/2015 | Anantha et al. | |
| D739,885 S | 9/2015 | Lee et al. | |
| D740,863 S | 10/2015 | Kemperle et al. | |
| D745,069 S | 12/2015 | Kemperle et al. | |
| D745,903 S | 12/2015 | Armani | |
| 9,473,760 B2 | 10/2016 | Buser et al. | |
| 9,499,779 B2* | 11/2016 | Murphy | C12M 29/00 |
| 2003/0175410 A1 | 9/2003 | Campbell et al. | |
| 2006/0156978 A1* | 7/2006 | Lipson | A61L 27/36 118/708 |
| 2006/0225834 A1* | 10/2006 | Medina | B29C 67/0059 156/273.3 |
| 2010/0208006 A1 | 8/2010 | Seilenfreund | |
| 2011/0212501 A1 | 9/2011 | Yoo | |
| 2012/0089238 A1 | 4/2012 | Kang et al. | |
| 2014/0117585 A1* | 5/2014 | Douglas | B33Y 30/00 264/401 |
| 2015/0037445 A1* | 2/2015 | Murphy | B29C 64/386 425/131.1 |
| 2015/0059798 A1* | 3/2015 | Mazed | A45D 20/50 132/272 |
| 2015/0105891 A1* | 4/2015 | Golway | G06F 17/50 700/98 |
| 2015/0142159 A1* | 5/2015 | Chang | B29C 67/0007 700/119 |
| 2016/0083516 A1* | 3/2016 | Elomaa | C08L 77/04 525/54.1 |
| 2016/0288414 A1* | 10/2016 | Ozbolat | B41J 3/407 |
| 2016/0367358 A1* | 12/2016 | Tran | A61L 27/60 |
| 2017/0182717 A1* | 6/2017 | Byun | B22F 3/008 |
| 2018/0002658 A1* | 1/2018 | Miller | C12M 3/00 |
| 2018/0186076 A1* | 7/2018 | Backer | B33Y 80/00 |
| 2018/0281280 A1* | 10/2018 | Solorzano | B29C 64/209 |
| 2019/0225824 A1* | 7/2019 | Hsu | A61L 27/26 |

FOREIGN PATENT DOCUMENTS

| | | |
|---|---|---|
| WO | WO-2010-030964 A2 | 3/2010 |
| WO | WO-2013-158508 A1 | 10/2013 |

OTHER PUBLICATIONS

Gramlich, W. et al., "Transdermal gelation of methacrylated macromers with near-infrared light and gold nanorods", Nanotechnology, Dec. 1, 2013, 25(1), 8 pages.

International Patent Application No. PCT/US2015/022458; International Search Report dated Mar. 25, 2015, 27 pages.

\* cited by examiner

A

B

C

D

A

B

C

| Syringe A Contents | Syringe B Contents |
|---|---|
| 160 Viscosity Agent + 162 Polymer + 164 Photo-Initiator + 166 Cells | N/A |
| 162 Polymer + 164 Photo-Initiator + 166 Cells | 160 Viscosity Agent |
| 162 Polymer + 164 Photo-Initiator | 160 Viscosity Agent |

FIG. 16

METHODS, DEVICES, AND SYSTEMS FOR THE FABRICATION OF MATERIALS AND TISSUES UTILIZING ELECTROMAGNETIC RADIATION

CROSS REFERENCE TO RELATED APPLICATIONS

This application is a US national stage of International Patent Application No. PCT/US2015/022458, filed Mar. 25, 2015, which claims the benefit of the priority of U.S. Provisional Patent Application No. 61/969,832, filed Mar. 25, 2014 and U.S. Provisional Patent Application No. 62/046,279 filed Sep. 5, 2014, which applications are incorporated by reference.

FIELD OF THE INVENTION

The disclosed invention is in the field of bioprinting materials utilizing electromagnetic radiation.

BACKGROUND

In today's age, machines have completely changed lives, ranging from the first computer to cellphones. However, the most precise and well-articulated systems remain those that nature has built. The human body is an example of one such system which remains to be re-engineered.

Organ transplantation has existed since the mid-1800s when the first skin transplant was performed. Since this time, transplantation has exploded, resulting in the transplantation of an organ or limb or even several organs/limbs simultaneously. Initially, organs only from living identical twins were transplanted. However, soon thereafter organs were transplanted from the living and deceased, providing that the patient and donor have close genetic similarities. The donors could be a family member or even a genetically compatible stranger. In fact, more than 600,000 transplants have occurred in the United States since 1988.

The quest for donor tissues and organs is a slow and uphill battle. Simply stated, there are not enough donor tissues and organs and more than 6,000 people die each year due to organ failure. There are presently over 120,000 people in the US alone on waiting lists for organs and others experiencing chronic problems due to the long-term damaging effects of post-transplant immunosuppression. This has prompted significant research and tests on fabricating mechanical organs and transplanting tissue and organs from non-humans, neither of which has had much success. Unfortunately, the need for donor tissues and organs has also resulted in the black-market sale of tissues and organs from both willing and unwilling individuals.

Donor tissues, organs, and even animals are also used in the testing and evaluation of pharmaceutical drugs. In fact, in bringing a pharmaceutical drug to the market, it takes years, even decades of animal testing before clinical trials on humans may be performed. Not only do some have the view that animal testing is inhumane, but it is expensive and inefficient, particularly in situations where the pharmaceutical drug fails to make it to market.

Animal tissues and organs are incredibly complex, possessing multiple different compartments that communicate with each other, intricate microarchitecture within these compartments, and many different cell types within each compartment. Bioprinting involves recreating the 3D structure of a tissue using a fabrication technique where a computer program slices up a construct into discrete layers and rebuilds them using a biomaterial. These biomaterials are designed to mimic the architecture of the extracellular matrix in which cells are suspended. Additionally, cells themselves can be incorporated into these constructs. Accordingly, a complex organ may be built step-by-step using the 3D images, such as those from MRI and CT scans, native cells from a patient, and biologically compatible materials.

Thus, there is a need for devices, systems, and methods for bioprinting tissues and organs, without the need for donor organs in transplantation surgeries and animal testing in a number of industries. The invention is directed to these and other important needs.

SUMMARY OF THE INVENTION

In one aspect, a three-dimensional bioprinter is provided and includes a material deposition device comprising a cartridge for receiving and holding a composition containing biomaterial that cures after exposure to electromagnetic radiation (EMR) at or above 405 nm. The bioprinter also includes an EMR module that emits EMR at a wavelength of about 405 nm or higher.

In another aspect, an EMR module for a bioprinter is provided and includes an EMR source that emits EMR at or above 405 nm and exposes a composition to EMR.

In a further aspect, a cellular construct prepared using the bioprinter as described herein is provided.

In yet another aspect, a tissue construct is provided and contains an EMR responsive material and cells. The tissue construct is deposited using a bioprinter as described herein, exposing it to EMR at a wavelength of about 405 nm or greater.

In still a further aspect, a bioprinter cartridge containing cells and a material curable at a wavelength of about 405 nm or greater is provided.

In another aspect, a bioprinter cartridge is provided and includes (i) a chamber holding cells and a material curable at an EMR wavelength of about 405 nm or greater and an (ii) orifice through which the cells and material are extruded.

In a further aspect, a method for forming an array of cells is provided. The method includes supplying a composition containing biomaterial to a cartridge having an orifice through which the composition flows. The composition cures after exposure to EMR of a wavelength of about 405 nm or greater. The composition flows through the orifice onto a substrate.

In yet another aspect, a method of fabricating a tissue construct is provided. The method includes depositing a composition onto a support, wherein the composition contains cells and at least one extrusion agent which cures after exposure to EMR of a wavelength of about 405 nm or greater. The method also includes curing and/or incubating the composition for about 1 minute to about 1 year.

In still a further aspect, a kit is provided and includes (i) a first extrusion agent, (ii) a photo-initiator, and (iii) a second extrusion agent. The kit may also include a biomaterial.

In another aspect, a method of testing a chemical agent is provided and includes (i) applying the chemical agent to a cellular structure prepared using the bioprinter described herein; and (ii) measuring the viability of the cells in the cellular structure.

In a further aspect, a method for transplanting a synthetic organ in a mammal is provided and includes transplanting a cellular construct prepared using the bioprinter described herein to the mammal.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 16 is a diagram illustrating an embodiment of using multiple cartridges and the contents of two syringes.

DETAILED DESCRIPTION OF THE ILLUSTRATIVE EMBODIMENTS

Figure 1:
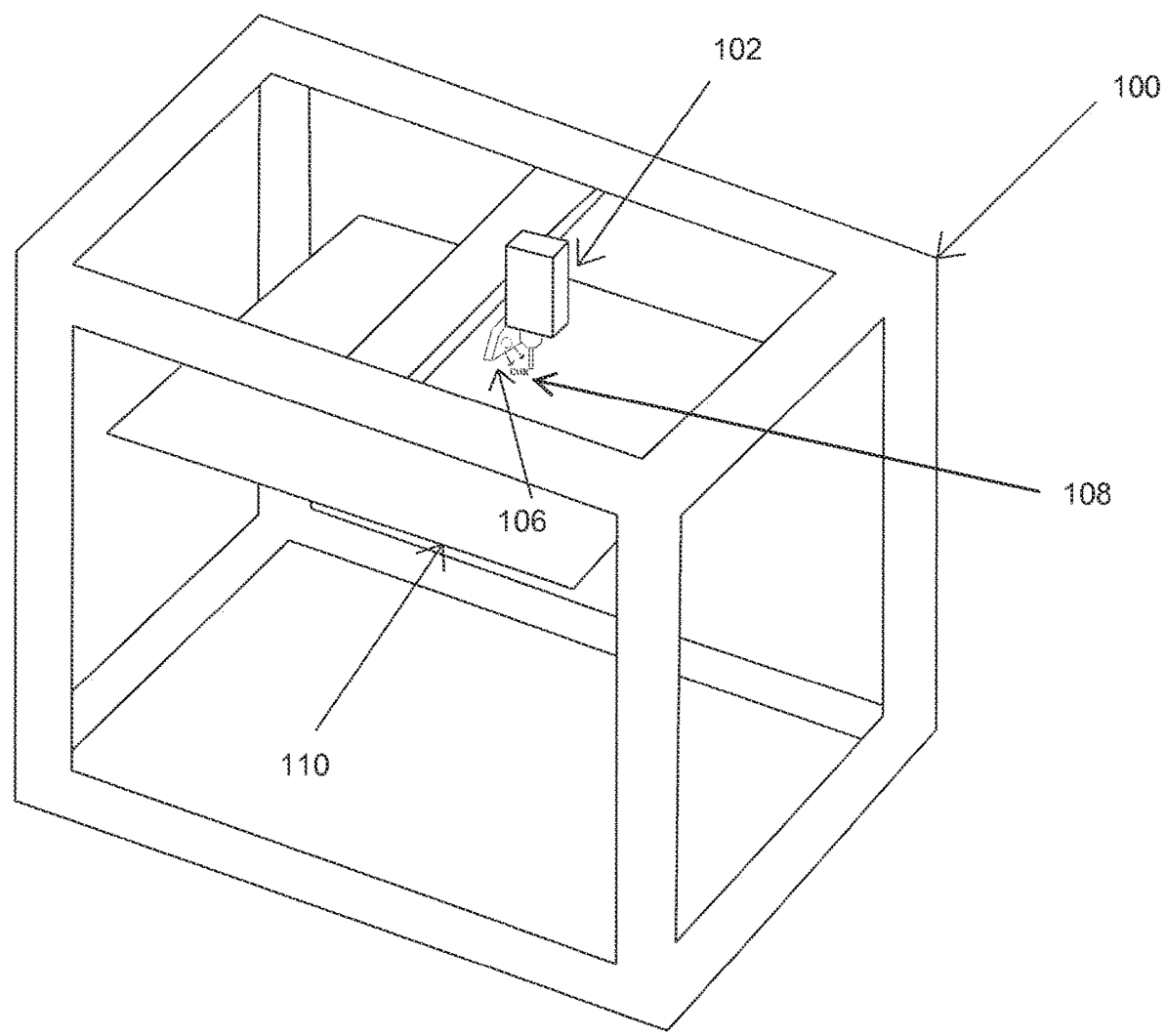
FIG. 1 depicts an embodiment of the bioprinter described herein having an emitter module and receiving plate.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the features and methods of making and using the coatings and films described herein.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such any combinations is considered to be another embodiment. Conversely, various features of the invention that are, for brevity, described in the context of a single embodiment, may also be provided separately or in any subcombination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

"Bioprinting" as used herein a three-dimensional, precise deposition of cells using an automated, computer-aided, three-dimensional prototyping device (e.g., a bioprinter).

The bioprinted cellular constructs, tissues, and organs are prepared using methods utilizing a rapid prototyping technology based on three-dimensional, automated, computer-aided deposition of cells. Advantageously, the bioprinters described herein are capable of generating organs and the like which do not result in an immune response and thus will not require the administration of an immunosuppressant for transplantation of an organ. The bioprinters also are uncontaminated and will not comprise any infectious agents such as viruses, bacteria, or the like. The bioprinters completely obviate the need for donor organs and are even cost effective since the organs are prepared from inexpensive biomaterials. The bioprinters also reduce or eliminate the need for animal testing of any new chemical, including pharmaceutical agents.

A. Bioprinter

The bioprinter may include any instrument that automates the bioprinting process described herein. In one embodiment, the bioprinter is a 3D printer, which may be selected by one skilled in the art. Any component of the bioprinter described herein may be operated by manual or robotic means as determined by one skilled in the art.

The bioprinter contains one or more rods housed within the interior. In one embodiment, the rods may be placed at any direction or height and be of any width that is necessary to support one or more component of the bioprinter. In a further embodiment, the rods are placed along the x-axis, y-axis, or z-axis, or any combination thereof in the bioprinter. In another embodiment, the cartridge, receiving means, printer stage, or any combination thereof is attached to one or more rod. In a further embodiment, the cartridge moves along the x and y rods and the printer stage moves along the z rod.

The rods permit the receiving means to remain at the height needed to fabricate the article. The rods may also be utilized to calibrate and/or level one or more component of the bioprinter. In one embodiment, the rods control movement of one or more component of the bioprinter including, without limitation, the cartridge, printer stage, or any combination thereof. The movement of the rods may be performed using skill in the art including, without limitation, a motor.

The rods housed within the bioprinter may also include endstops. The endstops are a means of defining a boundary to build the fabricated article. The endstops are also useful to keep one or more component of the bioprinter in a particular position. The endstops may contribute to calibrating the position of one or more component on the respective x, y, and/or z rod. In one embodiment, the endstops ensure that the cartridge stays within the area of the receiving means. In another embodiment, the x and y endstops define the boundary for the cartridge. Accordingly, the x and y endstops restrict the movement of the cartridge to the size of the receiving means. For example, the cartridge may hit an endstop and cannot proceed past this point, i.e., it stays within the area of the receiving means. In a further embodiment, the z endstop defines the boundary for the receiving means and/or printer stage. Accordingly, the z endstop assists in modulating the height of the receiving means. In this instance, the z endstop ensures that the printer stage and receiving means do not move too high. In doing so, the z endstop may prevent the receiving means from contacting the needle and damaging the syringe and/or destroying the fabricated article. The endstops may be fabricated using any materials available in the art including, without limitation, glass, coated glass, plastic, coated plastic, metal, a metal alloy, gel, or any combination thereof.

As noted above, one or more component of the bioprinter may be calibrated prior to or at one or more times during the bioprinting. Accordingly, the bioprinter contains a calibrating means for obtaining the proper level for one or more component. In one embodiment, one or more of the cartridge, printer stage, receiving means, among others, is calibrated. In another embodiment, one or more component of the bioprinter is calibrated along one or more of the x, y, and z axes. Calibration of the bioprinter may be performed using manual techniques, automated techniques, or a combination thereof. In one embodiment, the calibration means may include laser alignment, optical alignment, mechanical alignment, piezoelectric alignment, magnetic alignment, electrical field or capacitance alignment, ultrasound alignment, or any combination thereof.

The procedure for calibrating one or more component of the bioprinter includes use of the above-noted rods. The one or more component of the bioprinter is attached to one or more rod by one or more screw. In one embodiment, the receiving means and the printer driver are attached to the same rod or rods. In another embodiment, the receiving means and printer driver are attached to a single x axis rod. In a further embodiment, the receiving means and printer driver are attached to the rod using one or more screw. In yet a further embodiment, the receiving means and printer driver are attached to the rod using three screws. In still another embodiment, one or more screws pass through the receiving means and printer driver and are secured on the underface of the printer driver. In yet a further embodiment, the one or more screw is secured using means in the art including a wingnut. To facilitate the adjustment, a spring may be placed between the receiving means and printer drive. The selection of the spring is within skill in the art. In one embodiment, the spring is metal, plastic, or the like. In another embodiment, the spring is zinc plated. In a further embodiment, the spring is a zinc plated music wire. The length and diameter of the spring depends on the size of the bioprinter, components therein, and article being fabricated. In one embodiment, the length of the spring is about 1 mm to about 75 mm. In a further embodiment, the length of the spring is about 10 to about 30 mm. In another embodiment, the diameter of the spring is about 1 to about 10 mm. In yet a further embodiment, the screw passes through the spring. The location of the receiving means along the x, y, and z axes may be adjusted by tightening and loosening, i.e., screwing or unscrewing, the wingnuts.

In order to prepare the fabricated materials, the bioprinters disclosed herein dispense the composition with repeatable accuracy. In one embodiment, the position of the cartridge is calibrated along the x-axis, the y-axis, and the z-axis, or any combination thereof. The accuracy is dependent on a number of factors, including, without limitation, removal and insertion of cartridges, position of the cartridge, among others. Calibrating the position of the cartridge includes the use of a laser, may be manual (e.g., visual), or any combination thereof.

The atmosphere of the bioprinter may also be adjusted to provide the optimal conditions for depositing the composition. Specifically, the temperature, humidity, atmospheric composition, among others may be varied. In one embodiment, the bioprinter may include a means for adjusting temperature of the bioprinter, in general, or of the individual components therein including inside the cartridge, the receiving means, or the atmosphere of the bioprinter in general. The selected temperature may be selected by one skilled in the art and may depend on the type of cell being printed. In one embodiment, the temperature is maintained at a temperature which results in a suitable physical environment for the cells. In one embodiment, the temperature is maintained at about −10 to about 300° C. In a further embodiment, the temperature is maintained at about 0 to about 100° C. In another embodiment, the temperature is maintained at about room temperature. In another embodiment, the temperature is maintained at about 37° C. The means may include a heating or cooling element. Heating elements include, without limitation, radiant, convection, conductive, fan, heat exchange heater, or any combination thereof. The cooling element may including, without limitation, coolant, chilled liquid, ice, a radiant cooler, convection cooler, a conductive cooler, a fan cooler, or any combination thereof.

The humidity of the bioprinter in general or of the individual components including inside the cartridge may also be varied as discussed above. Specifically, the humidity may be increased or decreased as necessary. Humidities ranging from about 0% to about 100% may be utilized.

The gaseous composition of the bioprinter, when sealed, further may be varied. In doing so, gases aside from air including varying concentrations of carbon dioxide, nitrogen, argon, and oxygen may be utilized and varied as needed.

Also contemplated is a means for applying a wetting agent to one any one or more part of the bioprinter as described below including, without limitation, the receiving means, cartridge, cartridge contents, or any combination thereof. The "wetting agent" includes a fluid which facilitates extrusion of the composition described herein, prevents the fabricated article from adhering to the receiving means, among others. In one embodiment, the wetting agent is hydrophilic or hydrophobic. In another embodiment, the wetting agent is, without limitation, water, tissue culture media, buffered salt solutions, serum, or any combination thereof. The wetting agent may be applied before, simultaneously, or after the composition is dispensed.

B. Printer Stage

A printer stage is another component of the bioprinter described herein. The printer stage as used herein regulates the movement of the receiving means, as described above. In one embodiment, the printer plate moves the receiving means up and down. The printer stage may be, without limitation, glass, coated glass, plastic, coated plastic, metal, a metal alloy, gel, or any combination thereof. In one embodiment, the printer stage is square, circular, triangular, oval, rectangular, or irregularly shaped.

The printer stage is located within the bioprinter and adjacent to the receiving means. In one embodiment, the printer stage is positioned below the receiving means.

C. Receiving Means

The bioprinter is capable of dispensing composition in predetermined geometries, i.e., positions, patterns, layers etc., in two or three dimensions, onto a means for receiving the composition. In one embodiment, the receiving means is a receiving plate. In another embodiment, the receiving means is a 3-D structure such as a limb, organ, tissue, gel, multi-well plate, or any combination thereof. In a further embodiment, the receiving means is a water bath. In one embodiment, FIG. 1 is a top view of a bioprinter 100 described herein. Cartridge 102 includes a means for receiving and holding a composition. EMR module 106 emits EMR 108, exposing the contents on receiving plate 110. Receiving plate 110 receives the deposited material.

Figure 2:
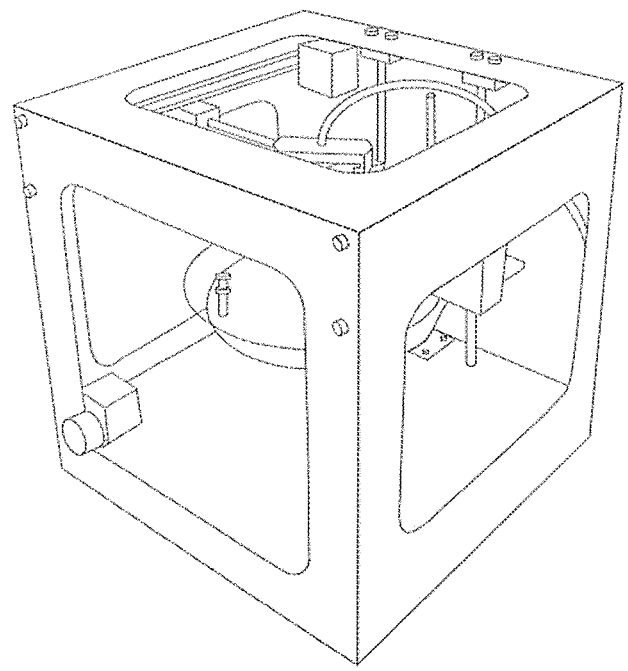
FIG. 2 illustrates an embodiment of 3D bioprinter described herein that has a 3 axis system on which devices can move.
Figure 2:
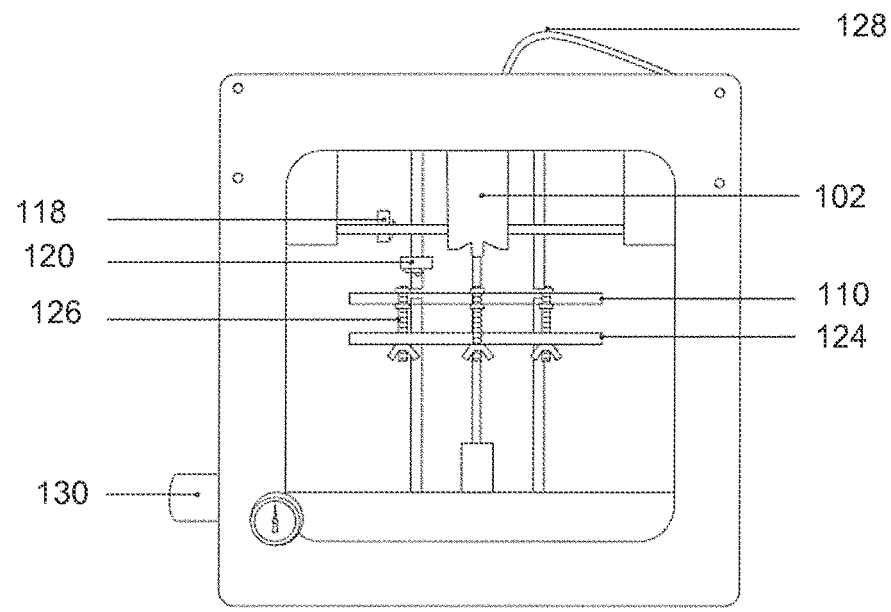
Figure 2:
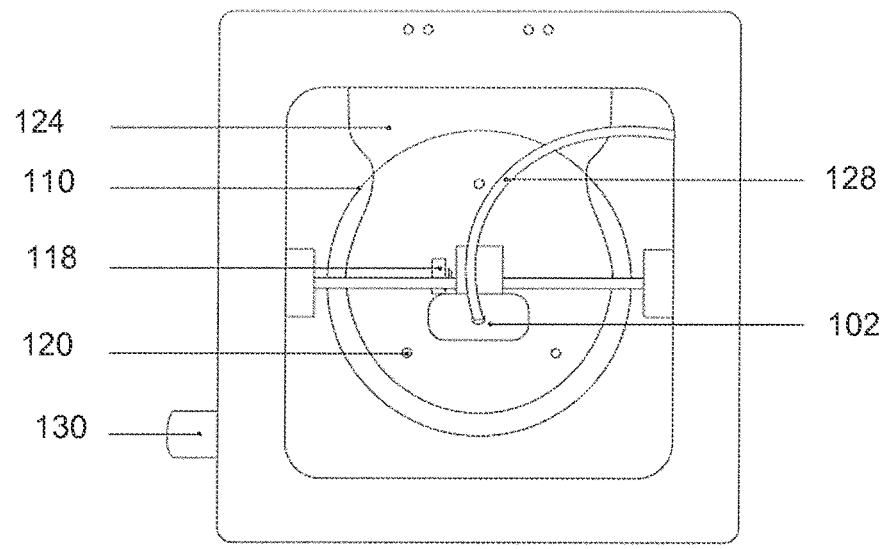
Figure 2:
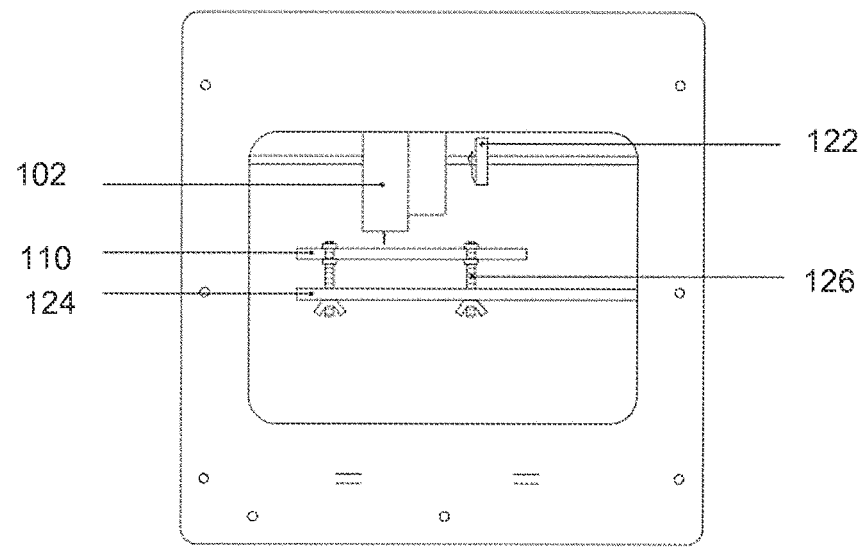
Figure 2:
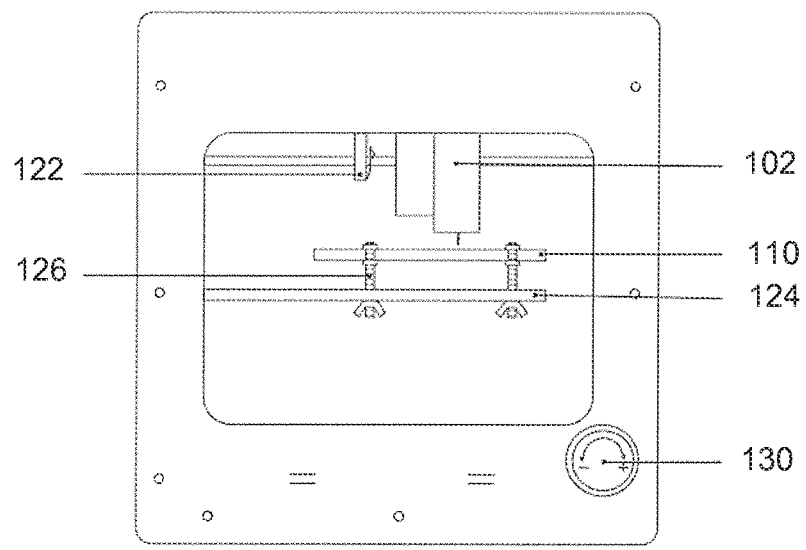

Another embodiment of a bioprinter described herein is presented in FIG. 2. FIG. 2A is an edge-view of the bioprinter illustrating a 3 axis system on which devices can move. FIG. 2B is a side-view of the bioprinter having cartridge 102 and receiving plate 110. This printer is programmed to move in 3D space by zeroing itself with endstops 118 and 120. Receiving plate 110 can be leveled using a spring-based system 126 and printer driver 124. For example, in this case, the bioprinter uses pneumatic pressure 210 directed through conduit 128 to extrude materials. This pressure is controlled manually by dial 130. FIG. 2C is a top-view of the bioprinter of FIG. 2B. FIG. 2D is a second side-view of the bioprinter, but showing endstop 122. FIG. 2E is 180° side-view of the bioprinter of FIG. 2D.

Accordingly, the bioprinter achieves a particular geometry of the fabricated article by moving the cartridge relative to a receiving means. Alternatively, the receiving means is moved relative to the cartridge.

In an effort to reduce contamination, the receiving means is non-toxic to the biomaterial, components of the composition, or any combination thereof. The locations at which the bioprinter deposits the composition onto a receiving means are adjustable as determined by the user.

The receiving means is desirably designed specifically to accommodate the shape, size, texture, or geometry of the fabricated article. It may be may be flat or substantially flat; smooth or substantially smooth; defined or substantially defined; or any combination thereof. The receiving means may assume a variety of concavities, convexities, or topographies based on the article to be fabricated. The receiving means may contain, without limitation, glass, coated glass, plastic, coated plastic, metal, metal alloy, gel, or any combination thereof. The receiving means and the biomaterial may be biocompatible. In one embodiment, the receiving means is a substantially flat plate, multi-well plate such as a 6- or 96-well plate, or 3D scaffold in which the cartridge moves 3 dimensionally. In another embodiment, the receiving means is square, circular, triangular, oval, rectangular, or irregularly shaped.

The receiving means is located within the bioprinter and adjacent to the cartridge. The receiving means may also be adjacent to the printer stage. In one embodiment, the receiving means is positioned below the cartridge. In another embodiment, the receiving means is positioned above the printer driver. In a further embodiment, the receiving means is positioned between the cartridge and the printer stage.

The receiving means may be leveled prior to deposition of the composition. The leveling may be performed as described above by adjusting the printer stage using the rods and endpoints. Alternatively, the bioprinter could have a self-leveling means, thereby eliminating the need for human intervention for leveling the hardware. In doing so, software may be used to analyze the position of the receiving means and perform any necessary adjustments. In one embodiment, the receiving means is leveled to 0° relative to the flat bottom of the cartridge.

D. Cartridge

A "cartridge" is an object that is capable of receiving and holding a composition prior to deposition described herein. The cartridge may be attached to the bioprinter using any means known in the art. Any number of cartridges may be utilized and depends on the desired article for fabrication. In one embodiment, the cartridge is attached to the bioprinter through one of the aforementioned rods. In another embodiment, the cartridge is attached to a center piece which is attached to one or more rod. In a further embodiment, the cartridge is attached to a center piece along the x-rod.

In one embodiment, one cartridge is utilized. In this instance, all of the components of the composition are combined in one cartridge.

In another embodiment, two or more, i.e., multiple cartridges may be utilized. In a further embodiment, 2 to about 25 cartridges may be used. In this instance, each cartridge contains the same composition or different compositions. For example, if using two cartridges, one composition may be deposited separately from the other composition by using a second cartridge. By doing so, the simultaneous or separate use of multiple cartridges may be used to create complex, hierarchical structures.

The cartridge may be attached to one or more additional cartridge. Alternatively, the cartridge is position separately from the other cartridges.

The cartridge is made from any material which may be used in the bioprinter described herein. In one embodiment, the cartridge is glass, plastic, metal, gel, or any combination thereof. The cartridge may be coated on its interior or exterior with a casing. The casing may be made from any material that is compatible with the cartridge and includes glass, metal, plastic, or any combination thereof. The casing may be the same material as the cartridge or different.

Figure 3:
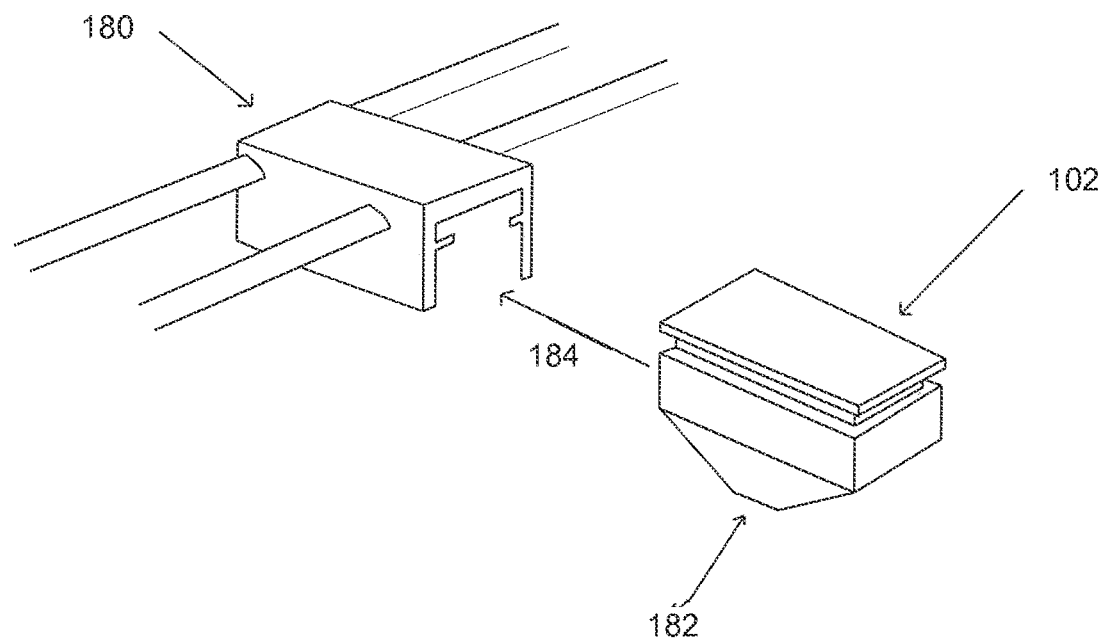
FIG. 3 illustrates a connecting means for connecting a cartridge to a bioprinter described herein.

The cartridge is of any shape which fits into the bioprinter and may be selected by one skilled in the art. In one embodiment, the cartridge is cylindrically shaped. In another embodiment, the cartridge is graduated at one end, i.e., one end is triangularly shaped and conicals downward. FIG. 3 illustrates a center piece 180 for attaching cartridge 102 to a bioprinter described herein. Cartridge 102 is cylindrically shaped and contains grooves for insertion of cartridge 102 and orifice 182. Cartridge 102 is slid into center piece 180 along axis 184.

The cartridge contains a chamber and at least two openings. The cartridge has a capacity which is dependent of the selected fabricated article, composition, size of the dispensing means, among others. In one embodiment, the cartridge has a diameter of about 1 μm to about 10 mm. In another embodiment, the cartridge has a diameter of about 1 to about 10 mm. In a further embodiment, the cartridge has a capacity of at least about 0.1 mL. In another embodiment, the cartridge has a capacity of about 0.1 mL to about 5000 mL. In still a further embodiment, the cartridge has a capacity of about 1 mL to about 100 mL. In yet another embodiment, the cartridge has a capacity of about 1 to about 20 mL.

Figure 4:
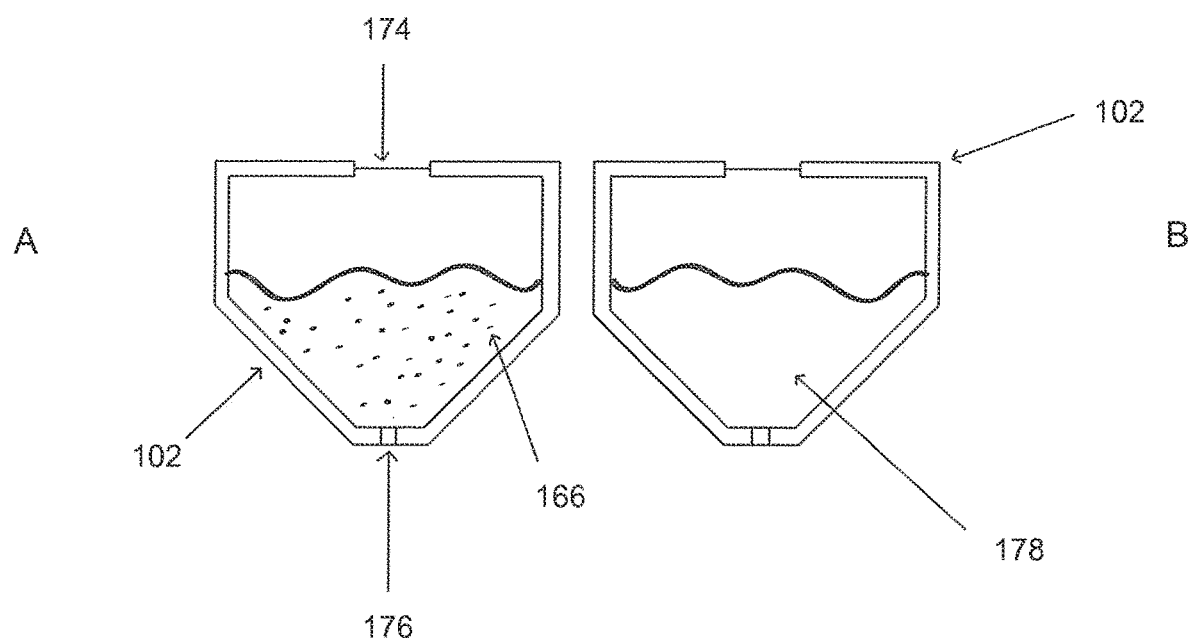
FIG. 4 is one embodiment of a cartridge containing one or more EMR module described herein.

In one embodiment, the cartridge contains one opening at one end and a second opening at the opposite end. In another embodiment, the cartridge contains one opening which permits insertion of a dispensing means into the chamber. In a further embodiment, the cartridge contains a second opening which permits a portion of a dispensing means, i.e., the needle, to exit the cartridge. The size of the first and second openings depends on the dispensing means utilized in fabrication of the article. In one embodiment, the first and second openings are, independently, about 1 μm to about 10 cm. In another embodiment, the first and second openings are, independently, about 2 to about 10 mm. FIG. 4 depicts a cartridge that holds and deposits the composition. FIG. 4A is cartridge 102 containing a composition containing biomaterials 166. The upper portion 174 of cartridge 102 generates the force, current, or temperature differential to permit deposition of the composition through extrusion orifice 176. FIG. 4B is a second cartridge 102 containing the components of FIG. 4A, but having a solid material 178 contained therein.

The cartridge also may be open to atmospheric conditions of the room or closed to atmosphere conditions (i.e., open only to the atmospheric conditions of the bioprinter). Any opening of the cartridge may be temporarily or permanently sealed. The cartridge is modifiable to hold different dispensing means. The tip of the dispensing means may be optionally capped to seal the components of the dispensing means from atmospheric pressure. In one embodiment, the cartridge and/or dispensing means is a closed system, i.e., limiting the exposure of the user to the specific contents in the cartridge. In another embodiment, the cartridge and/or dispensing means is an open system for compositions that are sufficiently viscous to drive deposition without the need for exogenous methods. In one embodiment, the cartridge is sealed using a cap or lid which adaptable to the particular cartridge being utilized. In another embodiment, the lid provides the mechanism for attaching the cartridge to the bioprinter. Accordingly, the cap or lid may include a first portion which attaches to and seals the cartridge and a second portion which attaches to a bioprinter. In one embodiment, the lid attaches to a center piece of the bioprinter.

The center piece of the bioprinter, as noted above, secures the cartridge to the bioprinter. The cartridge is designed so as to be physically compatible with the center piece and contains an opening into which the cartridge may be placed/inserted.

Figure 5:
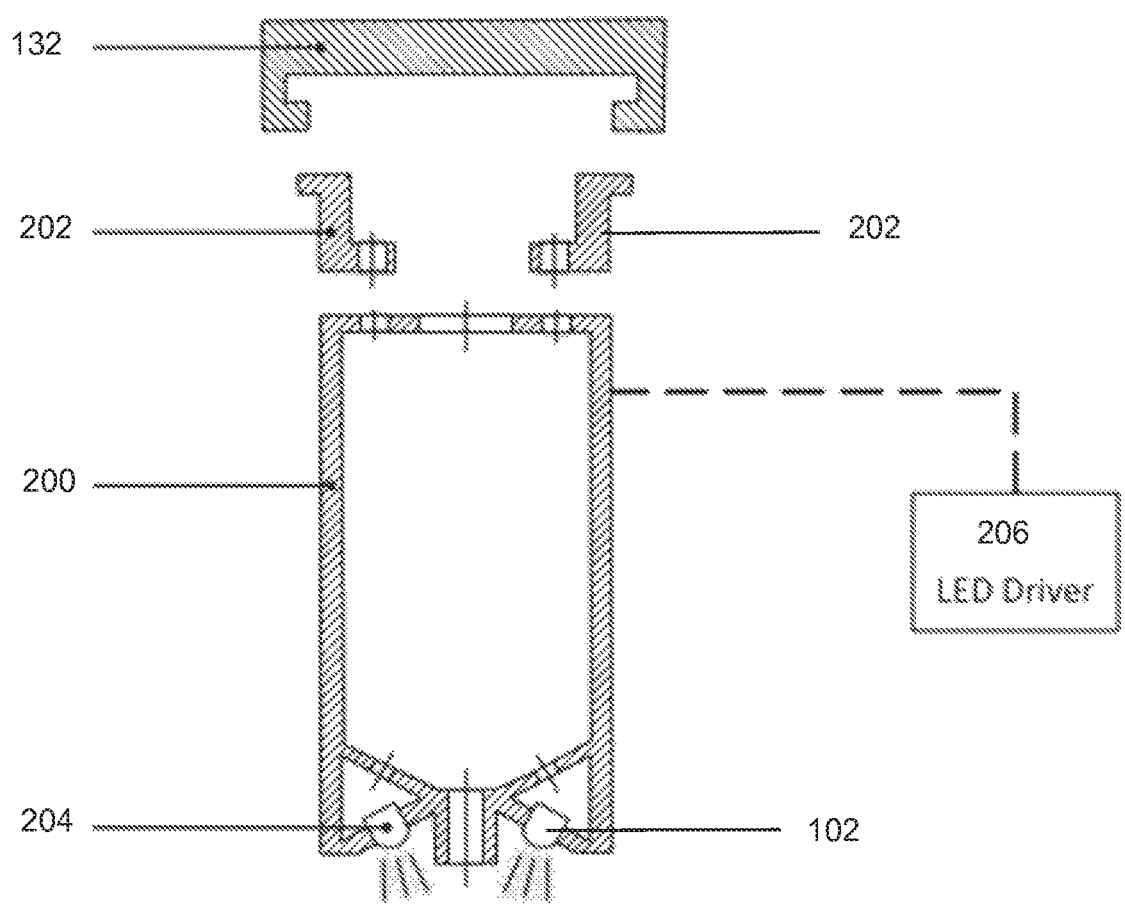
FIG. 5 is an embodiment of a cartridge described herein that holds one or more compositions described herein.

The cap of the cartridge may attach directly to the cartridge of may attach thereto via one or more cap holders. The cap holder(s) attach to the cartridge. The cap is also compatible with the cap holder and securely fit together to substantially seal the cartridge. In one embodiment, the cap, cap holder, and the cap/cap holder secured together have grooves and ridges, i.e., a specific shape. Conversely, the center piece has the opposite grooves and ridges to that of the cap, cap holder, and/or cap/cap holder secured together. FIG. 5 is one embodiment of a cartridge of the bioprinter described herein. Cartridge 102 contains casing 200, two cap holders 202, and the lid/cap 132 that locks the syringe in place. The bottom of the cartridge contains two LEDs 204 that are housed inside compartments. The LEDs are connected in series and are controlled by an LED driver 206.

Figure 6:
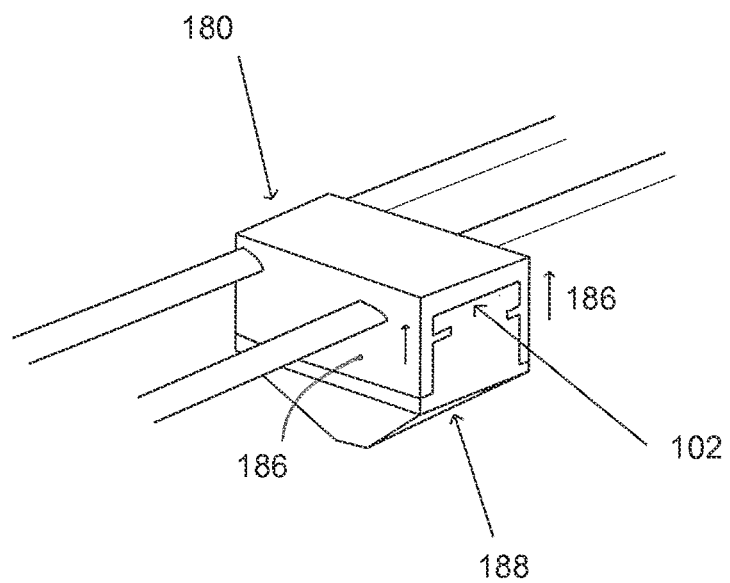
FIG. 6 illustrates a connecting means holding a cartridge for a bioprinter described herein.

FIG. 6 depicts center piece 180 directly adjacent to cartridge 102 of FIG. 5. Compression 186 creates a seal between center piece 180 and cartridge 102 to ensure proper deposition of the inner contents. A manual or automated system 188 creates the connection between cartridge 102 and center piece 180.

The cartridge is secured into the center piece using skill known in the art. In one embodiment, the cartridge is secured into the center piece using mechanical force, electromagnetic force, or pressurized force. In another embodiment, the cartridge is secured into the center piece using one or more latch. In a further embodiment the cartridge is secured into the center piece using magnetic attraction, collet chuck grip, ferrule, nut, barrel adapter, or any combination thereof. The cartridge may be clipped or snapped in (manually or with magnetic force) or a robotic arm can be used to replace each cartridge in the limited number of cartridges as the printing proceeds. Compression may be applied to the center piece, cartridge, or any combination thereof to create a seal. In one embodiment, the seal prevents unwanted gases or solid particles from entering the cartridge. In another embodiment, the seal assists in the deposition of the composition. The compression may be applied manually or may be automated.

The bioprinter may also include a sensing means for sensing if the cartridge is locked into the center piece. In one embodiment, the sensing means is a magnetic sensor, electrical signal, mechanical switch, or any combination thereof. The sensing means may further include an alert if the cartridge is not locked into the center piece. In one embodiment, the sensing means is a light sensor, alarm, or any combination thereof. In another embodiment, the alert is generated using a light gate or motion sensor.

The cartridge may be permanently or temporarily marked (pen or sticker), colored, dyed, scored, painted, polished, or any combination thereof. The cartridge may be uncovered, partially covered or fully covered using any means known in the art. In one embodiment, the cartridge prevent the contents therein from being prematurely exposed to the EMR (i.e., exposed to light). In another embodiment, the cartridge is covered to present premature EMR exposure. In a further embodiment, the cartridge is impermeable to light having a wavelength of about 405 nm or greater. In doing so, the covering prevents the composition from curing in the cartridge and jamming the dispensing means, i.e., the syringe. Any part of the cartridge may be covered including, without limitation, the entire cartridge, the tip of the cartridge, a portion of the cartridge, or any combination thereof. In another embodiment, the cartridge is covered using aluminum foil, adhesive foil, a plastic film such as a Parafilm® coating, or the like.

E. Dispensing Means

The cartridge utilized herein houses and protects a dispensing means. Many types of dispensing means are suitable for use with bioprinters disclosed herein and the methods of using the same. One of skill in the art would recognize that different dispensing means are required for different compositions containing biomaterial. For example, certain compositions may degrade plastic and, in that case, glass or metal dispensing means may be used.

The dispensing means contains one or more orifice through which the composition exits. In one embodiment, the dispensing means contains a single orifice. The orifice must be large enough to permit dispensing of the composition, but not too large as to have uncontrolled dispensing of the composition. The shape of the orifice is not a limitation and may be, without limitation, flat, circular, square, rectangular, triangular, oval, polygonal, irregular, smooth or textured. Accordingly, selection of a suitable orifice depends on the components and viscosity of the composition. In one embodiment, the orifice has a diameter of about 1 to about 1000 or more μm. In another embodiment, the orifice has a diameter of about 1 μm to about 100 μm.

Figure 7:
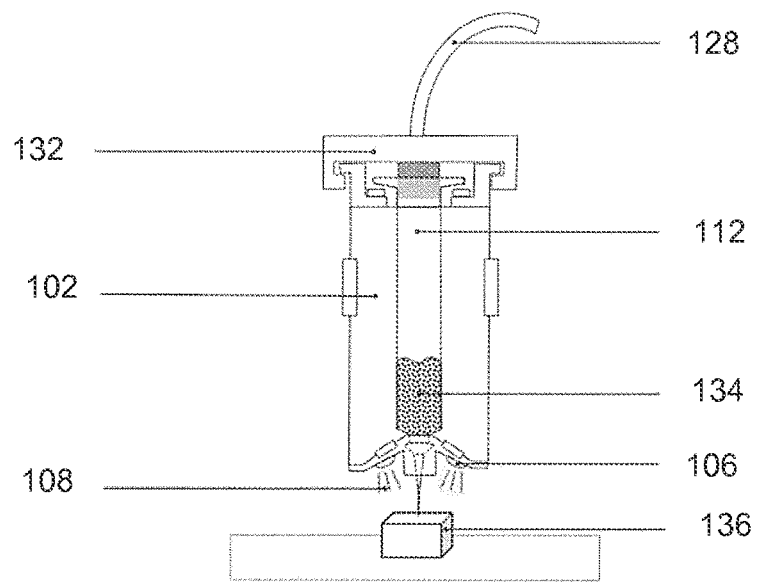
FIG. 7 illustrates an embodiment of a cartridge used in the methods, systems, and devices described herein.

The dispensing means may be a capillary tube, a micropipette, syringe or a needle. In one embodiment, the dispensing means contains a needle having a luminal diameter of about 10μ to about 5 cm. In another embodiment, the dispensing means contains a needle having a luminal diameter of about 1 mm to about 10 mm. In a further embodiment, the dispensing means contains a needle of about 1 mm to about 300 mm in length. In yet another embodiment, the needle is about 10 to about 100 mm in length. In still a further embodiment, the dispensing means is a Luer-Lok® Tip sterile syringe. In another embodiment, the dispensing means has a ⅕ mL graduation. In a further embodiment, the dispensing means has an about 6 mm (0.25") high precision tip FIG. 7 displays cartridge 102 used in this specific device. A syringe 112 is used to hold the composition for extrusion. Cap 132 is used to seal off syringe 112 from the atmospheric pressure and pneumatic pressure is transmitted to syringe 112 contents 134 using compressed air through conduit 128. The composition 134 within syringe 112 is deposited onto a receiving plate using EMR 108 from EMR module 106 into tissue structure 136.

Figure 8:
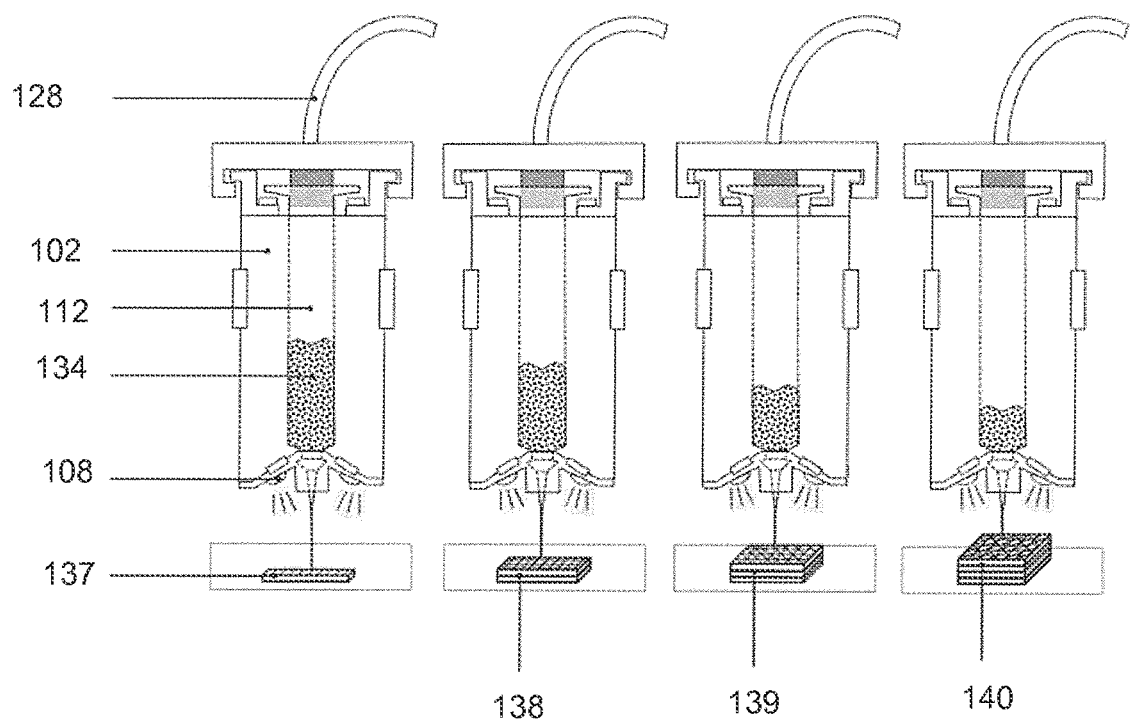
FIG. 8 illustrates an embodiment of fused deposition manufacturing via a multiple layering technique.

The embodiment presented in FIG. 8 illustrates the deposition of composition 134 layer by layer to create a 3D tissue via cartridge 102. EMR 108 chemically transforms composition 134 from a liquid state into a gel or solid state and binds layers together to create the construct. Air driven through conduit 128 puts pressure on composition 134 within syringe 112. Material is deposited layer-by-layer (layer 137, layer 138, layer 139) until tissue structure 140 is completed.

Figure 9:
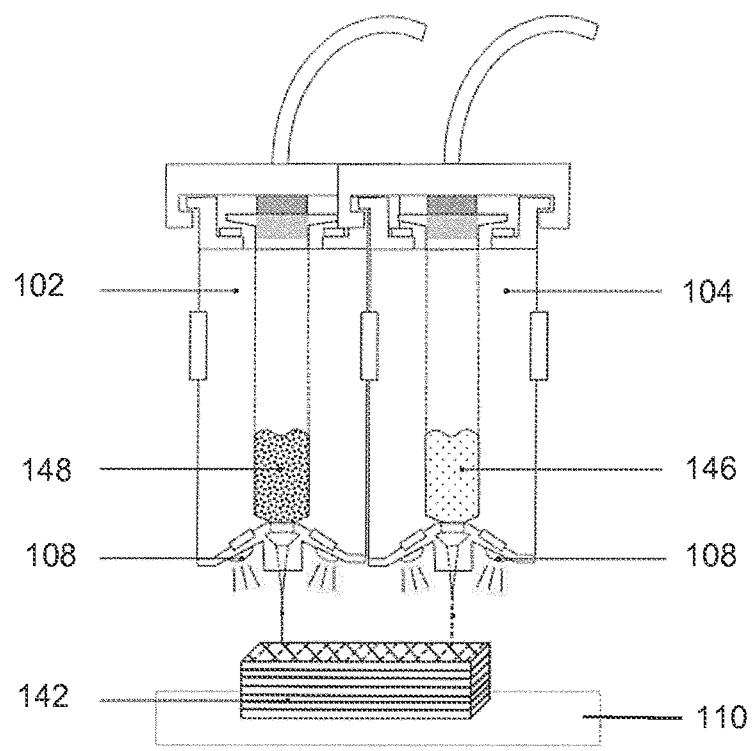
FIG. 9 illustrates an embodiment of the invention using multiple syringe heads.

FIG. 9 illustrates an embodiment of using multiple cartridges and syringes for extrusion. Multiple cartridges 102 and 104 are used to create tissue 142. Support material 148 from cartridge 102 is printed in layers and cells encapsulated in a second composition 146 in the next lattice or layer. Support material 148 hardens with EMR 108. Cartridge 102 with cell-laden composition 148 deposits its contents on receiving plate 110 and is solidified using EMR 108.

The contents of the dispensing means may be optionally primed prior to use to increase the accuracy of the process. The priming includes making the contents of the dispensing means ready to be dispensed.

The dispensing means may be disposable or permanent. In one embodiment, the dispensing means is ejected or removed, automated or manually, from the bioprinter following extrusion, dispensing, or deposition of the contents. In another embodiment, a new dispensing means is attached to the bioprinter. In a further embodiment, the cartridge is a premixed and pre-sealed cartridge which contains the necessary composition. By doing so, the user may purchase the cartridge and would not need to refill the dispensing means by preparing and adding the composition.

The dispensing rate of the dispensing means is dependent on one or more factors as determined by those skilled in the art. In one embodiment, the dispensing rate is dependent on the viscosity of the composition. In another embodiment, the dispensing rate is dependent on the pressure applied to the composition. In a further embodiment, the dispensing rate is high so that a fine line of composition may be deposited. In yet another embodiment, the dispensing rate is low so that a thicker line of composition may be deposited.

The dispensing means may be sealed for ease of use or to avoid contamination of the contents therein. Alternatively, the dispensing means are not sealed and may be opened by the user. In one embodiment, the dispensing means is sealed using cap which is permanently affixed to the dispensing means and cannot be pierced using a needle or the like. In another embodiment, the dispensing means is sealed using a cap which is permanently affixed to the dispensing means, but the cap may be pierced with a needle by the user. In a further embodiment, the dispensing means is sealed using a cap which may be easily removed by the user. In another embodiment, the dispensing means is impermeable to EMR of a wavelength of about 405 nm or greater.

F. Extrusion Means

The composition passes through the dispensing means using systems known in the art. In one embodiment, the composition is deposited onto the receiving means using gravity. In another embodiment, deposition of the composition may be facilitated via the use of an extrusion means. The term "extrude" or variations thereof as used herein refers to the ability of the composition to be forced to exit the dispensing means.

As one option, the extrusion means is a pressure means for controlling the pressure provided to the cartridge, dispensing means, or any combination thereof. The pressure may be generated using any system known in the art including, without limitation, pneumatic systems using compressed gas such as compressed air, argon, carbon dioxide, or nitrogen, hydraulics, pistons, screw-based means, or any combination thereof. The pressure required to deposit the composition depends on the article to be fabricated and contents of the composition, among others. In one embodiment, the pressure is about 50 to about 1500 kPa (about 0.1 to about 150 psi). In one embodiment, the compressor which directs the gas at the dispensing means and/or cartridge is connected to and operatively associated with the cartridge. By doing so, a controller and pressure pump is provided for the dispensing means. The pressure from the compressor drives deposition of the composition onto the receiving means. The pressure may be controlled using a dial operatively connected to the compressor. If more than one compressor is used, one dial may control the pressure of the compressor(s) or two or more dials may be utilized in an effort to obtain different pressures in different cartridges. In one embodiment, the compressed gas is fed into the cartridge and/or syringe using a hose. Each cartridge may utilize the same pressure to dispense the contents therein or use varying pressures.

Figure 10:
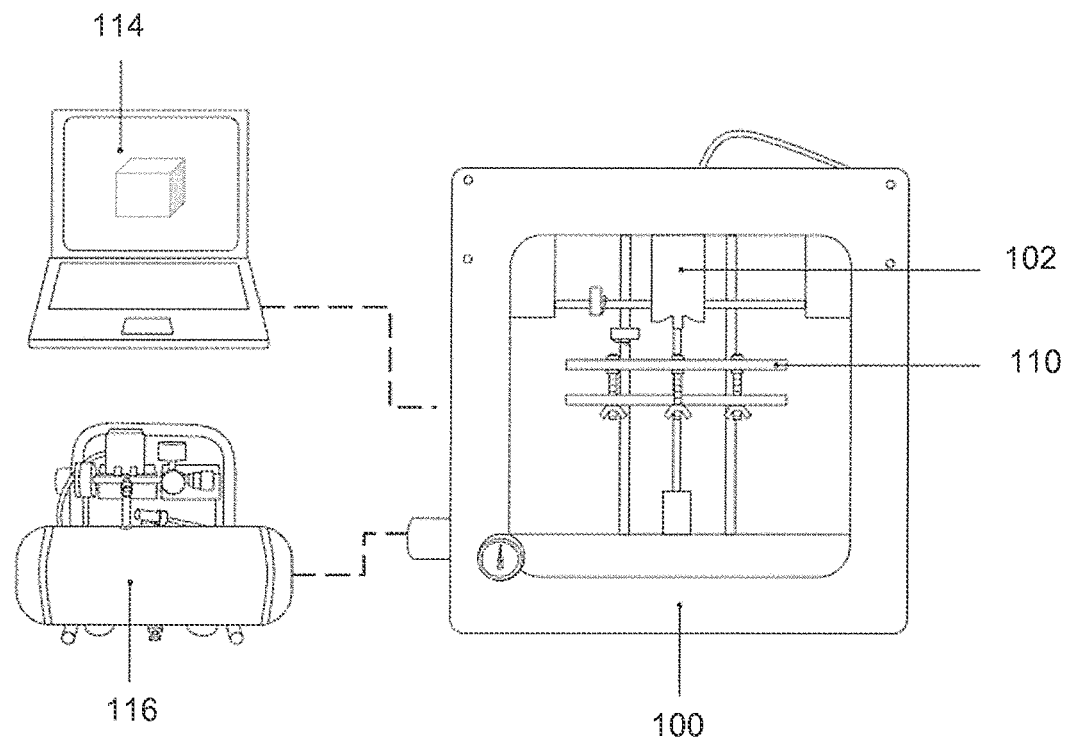
FIG. 10 illustrates an embodiment of an apparatus described herein which was used to create 3D tissue structures.

FIG. 10 is a schematic of a system and apparatus provided herein. The system includes computer 114, air compressor 116, and bioprinter 100. Air compressor 116 is connected to and operatively associated with cartridge 102 to provide a controller and pressure pump for the syringe. The pressure from air compressor 116 drives deposition of biomaterial onto receiving plate 110. All can be controlled by CAD software programmed in computer 116.

The extrusion means may also be thermal, electrical, piezoelectric, or mechanical as determined by those skilled in the art. In one embodiment, heat is applied to the composition, thereby reducing its viscosity. In another embodiment, the composition is electrically charged using a current. In a further embodiment, the composition is extruded using piezoelectric methods. In yet another embodiment, the composition is extruded using mechanical means such as a screw system to drive deposition.

G. EMR Source

The bioprinter includes an EMR module to cure the materials. The term "electromagnetic radiation" (EMR) as used therein refers to light having a wavelength of at least those in the visible spectrum. In one embodiment, the EMR is light in the visible spectrum. In another embodiment, the EMR is light in the near-infrared (NIR) spectrum. In a further embodiment, the EMR is in the infrared spectrum. In yet another embodiment, the EMR is about 405 nm or greater. In another embodiment, the EMR is about 405 nm to about 1 mm. In a further embodiment, the EMR is about 405 nm to about 700 nm. In still another embodiment, the EMR is about 1 mm to about 750 nm. In yet a further embodiment, the EMR is about 405 to about 410 nm.

The EMR module includes an EMR source that emits EMR at or above 405 nm and exposes a composition described herein to EMR. Many EMR sources are suitable for use with the EMR module described herein. In one embodiment, the EMR is a light emitting diode. In another embodiment, the EMR is an IR laser. One of more EMR source may be utilized to depending on the number of EMR modules utilized in the bioprinter. The EMR sources may be connected in series or in parallel.

The EMR module may include a chamber adjacent to the contents of the cartridge to EMR source. The EMR module may be separate from or permanently, semi-permanently, or reversibly attached to the bioprinter. In one embodiment, the EMR module is placed adjacent to the bioprinter so that the EMR is capable of reaching the composition. In another embodiment, the EMR module is physically attached or incorporated into the cartridge, i.e., the cartridge houses the EMR module. When the cartridge houses the EMR module, it may be on one side, multiple sides, inside, or outside of the cartridge.

The EMR is tunable with respect to wavelength, intensity, exposure time, or any combination thereof. In one embodiment, each EMR may be dimmed, brightened or focused depending on the curing required by the fabricated article. In a further embodiment, the EMR module contains an attenuation filter which lowers or raises the intensity of the EMR. In another embodiment, the EMR module is tuned based on the curing times, size, or any combination thereof which are required by the fabricated article. The EMR module may also be oriented to focus the EMR in any number of directions. By doing so, the EMR is accurately focused at the required position. The EMR module may be controlled using an EMR driver. In one embodiment, the total radiance of the EMR module is about 1 to about 10 mW/cm$^2$. In another embodiment, the total radiance of the EMR module is about 5 mW/cm$^2$.

The composition is exposed to the EMR for a period of time sufficient to cure the material. Suitable exposure times include 1 or more seconds. In one embodiment, the composition is exposed to the EMR for about 1 second to about 1 year.

Figure 11:
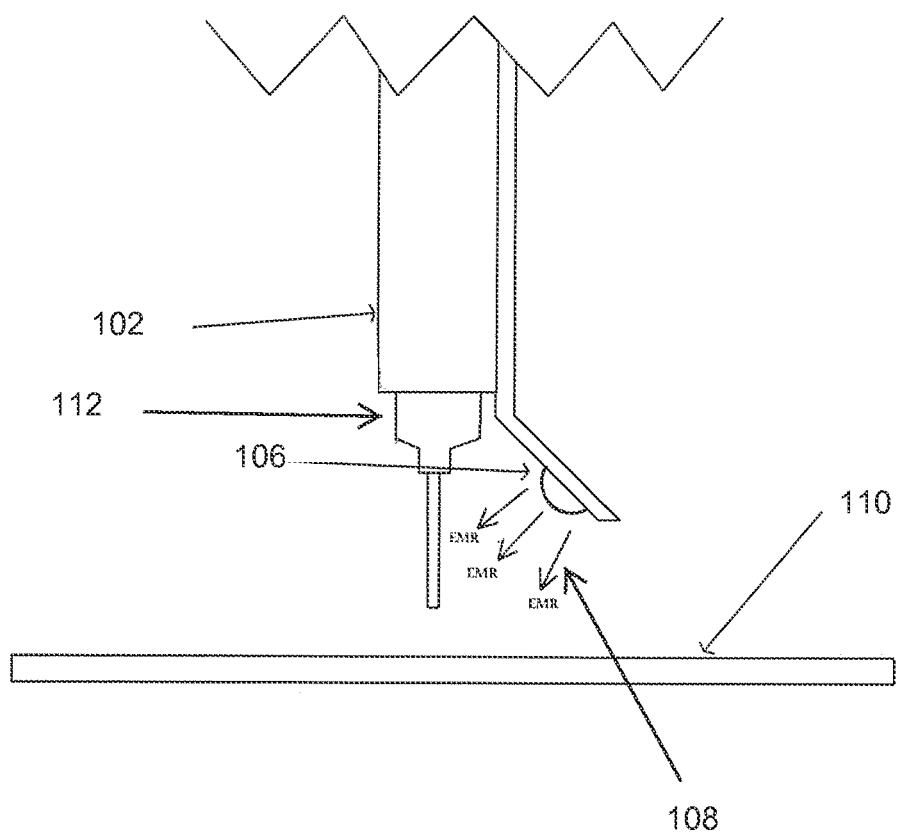
FIG. 11 illustrates one material deposition device having an EMR emitter module directing electromagnetic radiation (EMR) over a broad area towards the receiving plate.
Figure 12:
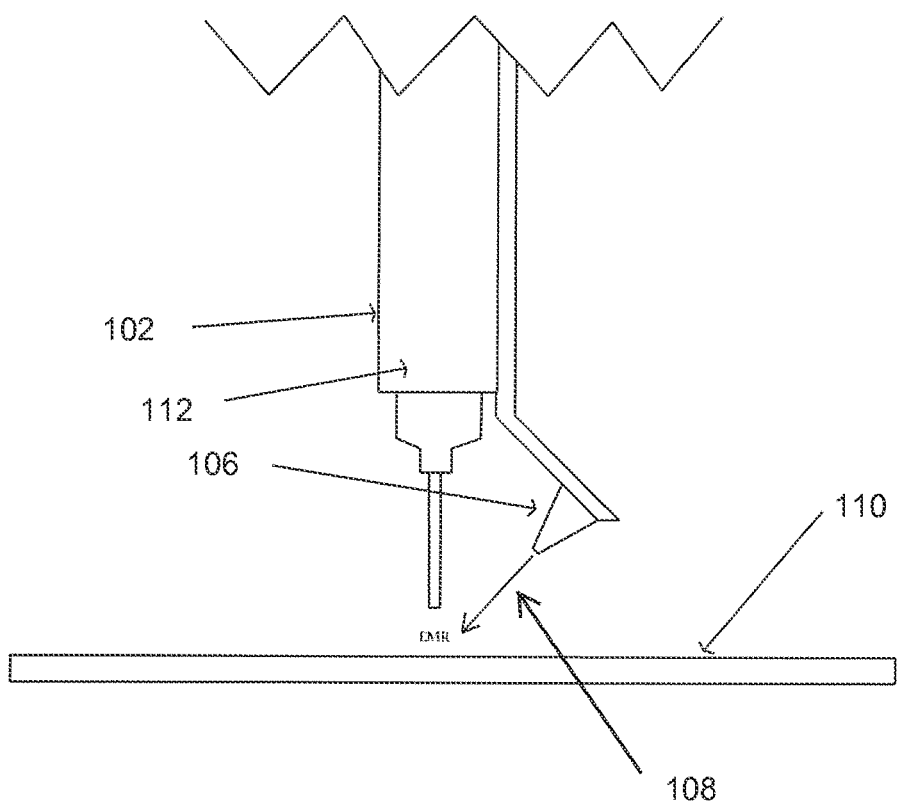
FIG. 12 depicts one material deposition device having an EMR emitter module directing the EMR to a specific location on the receiving plate to interact with the material upon, during, or after deposition.
Figure 13:
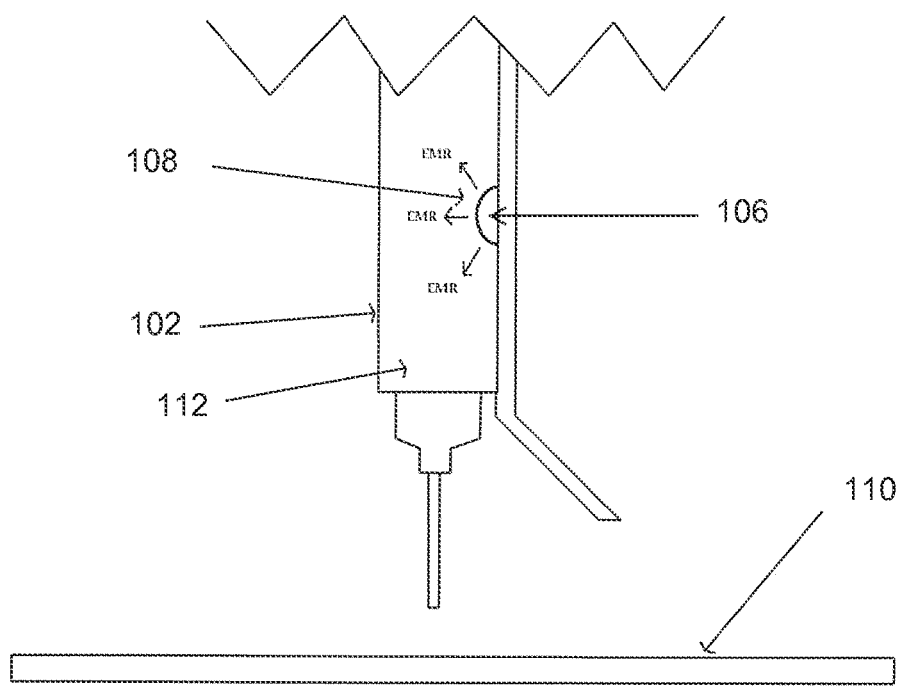
FIG. 13 illustrates an embodiment of a material deposition device having an EMR emitter module directing the EMR within the material device compartment to begin solidify the material before deposition and interaction with the receiving plate.
Figure 14:
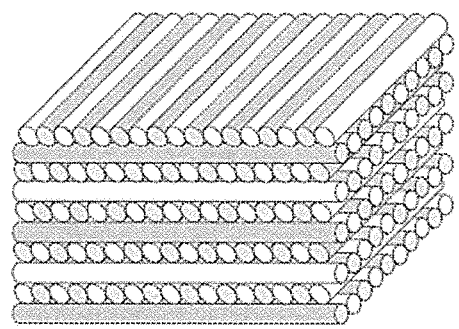
FIG. 14A illustrates a three-dimensional cell patterning of a two different materials to produce a single composite structure.
FIG. 14B depicts a cross sectional view of the structure and FIG. 14C depicts a top view of the structure demonstrating the lattice structure of the layered materials.
Figure 14:
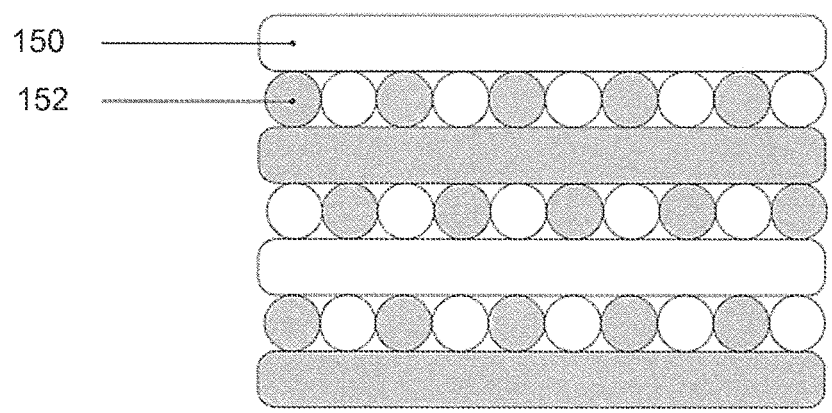
Figure 14:
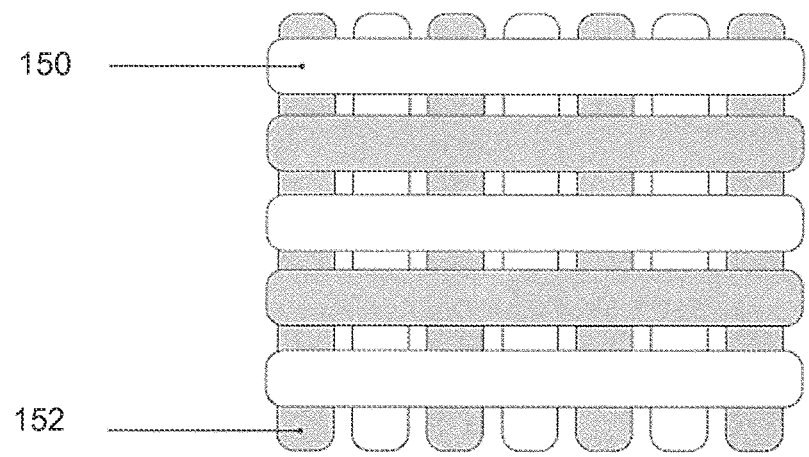

The EMR module is capable of exposing the biomaterials to EMR prior to, concurrently with, subsequent to, or any combination thereof to the dispensing. In one embodiment, the EMR is broadly directed in the vicinity of the deposition site. FIG. 11 is a side view of cartridge 102 having syringe 112 and EMR module 106 directing EMR 108 broadly towards receiving plate 110 to interact with the material upon, during, or after deposition. EMR module 106 emits EMR 108 broadly exposing the contents on receiving plate 110. In another embodiment, the EMR is specifically focused in one area on the deposition site. FIG. 12 is another side view of cartridge 102 having syringe 112 and EMR module 106 directing EMR 108 precisely towards a specific location on receiving plate 110 to interact with the material upon, during, or after deposition. In a further embodiment, the EMR is focused on at least one component of the composition being deposited. In yet another embodiment, the EMR is focused on the composition as it exits the deposition device. In still a further embodiment, the EMR module is contained within the cartridge and focuses EMR on the composition prior to deposition. FIG. 13 is a further side view of cartridge 102 having syringe 112 and EMR module 106 directing EMR 108 within the material device compartment to begin solidifying the material before deposition and interaction with receiving plate 110.

The EMR may also be sources of energy. In one embodiment, the EMR may be generated by interacting NIR light with gold nanorods to generate heat through the photothermal effect. In one embodiment, this EMR is generated in the presence of a thermal initiator. See, Gramlich, "Transdermal Gelation of Methacrylated Macromers with Near-infrared Light and Gold Nanorods," Nanotechnology, 25:014004, 2014 which is incorporated by reference.

There may be a single EMR module or may be several modules depending on the other components of the bioprinter and the fabricated article to be prepared. The EMR modules may all run at the same wavelength or may differ.

It is also contemplated that EMR modules may pulse going from bright to dim or dim to bright. In one embodiment, the EMR module pulses as each layer is printed.

H. Optical Device

The bioprinter described herein may optionally include an optical device for viewing the fabricated article. In one embodiment, the optical device contains a lens having a blue filter. By doing so, the fabricated article may be viewed and/or recorded without interference from the EMR, thereby providing increased quality control in monitoring and/or preparing the article. In another embodiment, the optical device is an optical recorder such as a camera, video camera, heat sensor camera, or any combination thereof. The optical device is at a resolution that is required for the particular composition being utilized and article being fabricated. Accordingly, the resolution of the optical device may be low, medium, or high, as determined by those skilled in the art.

The optical detector may be placed at any location of the bioprinter. In one embodiment, the optical device is placed in close proximity to the fabricated article. In another embodiment, the optical device is mounted on one or more component of the bioprinter or is adapted to move along side of the receiving means and/or cartridge. In a further embodiment, the optical device is mounted on the cartridge, receiving means, in the corner of the bioprinter, among others. In another embodiment, the optical device is mounted on the cartridge. In a further embodiment, the optical device is mounted adjacent to the receiving means. In yet a further embodiment, the optical device is mounted on the cartridge facing the receiving means. In still another embodiment, the optical device is adapted to move inside of the bioprinter by way of a track or the like.

The optical device may be temporarily or permanently attached to one or more component of the bioprinter. In one embodiment, the optical device is attached to the EMR module. In another embodiment, the optical device is permanently attached to the EMR module. In a further embodiment, the optical device is reversibly attached to the EMR module.

I. Software

The bioprinter deposits the composition at precise locations (in two or three dimensions) on the receiving means. The locations are dependent on the form being prepared and inputted information, which is translated into computer code. As known in the art, the computer code is a sequence of instructions, executable in the central processing unit (CPU) of a digital processing device, and written to perform a specified task. Additional bioprinting parameters including, without limitation, height of the cartridge, pump speed, robot speed, control of variable dispensing means, EMR exposure time, cartridge position, direction of the cartridge, and speed of the cartridge, among others.

Computer aided design software may be utilized to prepare the tissue constructs. In one embodiment, the software is 3D software. In another embodiment, the software is in the STL format. One of skill in the art would be able to select suitable software for use herein including 3DCrafter, 3DS Max, 3Dtin, Alibre, AC3D, Anim8or, Art of Illusion, AutoQ3D, AutoCAD, Blender, BRL-CAD, Cheetah3D, Cloud9, Creo Elements/Direct, DrawPlus, FormZ, FreeCAD, GLC Player, Google SketchUp, K-3D, LeoCAD, Maya, Magics, MeshLab, NetFabb, OpenSCAD, Rhino3D, Solidworks, STL-viewer, Tinkercad, Wings 3D, ZBrush, among others. The construct may be prepared from the top, bottom, or side as determined by one skilled in the art. In one embodiment, the construct is designed from the bottom.

The software may also be adapted to include code to modulate one or more component of the bioprinter. In one embodiment, the software modulates the flow of gas into the cartridge. In another embodiment, the software modulates the solenoid value that controls the flow of gas. In a further embodiment, the software controls the opening and closing of the solenoid value that controls the gas flow.

Alternatively or in conjunction, the tissue construct may be designed via reconstruction of tissues using medical imaging modalities. Examples of medical imaging modalities include, without limitation, Magnetic Resonance Imaging (MRI) and Computed Tomography (CT).

J. Non-Transitory Computer Readable Storage Medium

The devices, systems, and methods may further include non-transitory computer readable storage media or storage media encoded with computer readable program code. The computer readable storage medium may be connected to a bioprinter or removable from a digital processing device. Examples of computer readable storage medium include CD-ROMs, DVDs, flash memory devices, solid state memory, magnetic disk drives, magnetic tape drives, optical disk drives, cloud computing systems and services, among others.

K. Computer Modules

The devices, systems, and methods may include software, server, and database modules. As known in the art, "computer module" is a software component that interacts with a larger computer system, is one or more files and handles a specific task.

A computer module is optionally a stand-alone section of code or, optionally, code that is not separately identifiable. In some embodiments, the modules are in a single application. In other embodiments, the modules are in a plurality of applications. In some embodiments, the modules are hosted on one machine. In other embodiments, the modules are hosted on a plurality of machines. In some embodiments, the modules are hosted on a plurality of machines in one location. In other embodiments, the modules are hosted a plurality of machines in more than one location. Further described herein is the formatting of location and positioning data. In some embodiments, the data files described herein are formatted in any suitable data serialization format. A key feature of a computer module is that it allows an end user to use a computer to perform the identified functions.

L. Graphic User Interface

The computer module may include a graphic user interface (GUI) which provides a picture and/or text and may be 2- or 3-dimensional. The GUI may be a touchscreen or multitouchscreen. The GUI may include a grid comprising regularly spaced objects of substantially the same shape and substantially equal size.

The GUI may also be used to control one or more bioprinter parameter. In one embodiment, the GUI is used to control one or more components of the bioprinter. In another embodiment, the GUI is used to control the EMR, deposition speed, and/or temperature of one or more component, environmental conditions of one or more component, optical device, among others.

M. Components of the Composition

The tissues, organs, and vascular vessels may be prepared using the devices, systems, and methods described herein together with a composition. In one embodiment, the composition contains a biomaterial and optional additional components such as support material, non-cellular materials which enable bioprinting, or any combination thereof.

The composition may be prepared by mixing the cells and a biocompatible liquid or gel in a pre-determined ratio. The composition may optionally be treating to facilitate extrusion onto the receiving means, increase deposition efficiency, or initiate curing. In one embodiment, the composition is treated prior to extrusion to provide a desired cell density, provide a desired viscosity, among others using techniques known in the art. Such methods which may be utilized to prepare the composition for extrusion include, without limitation, centrifugation, tangential flow filtration, electrical conductance, light, or any combination thereof. The possible combinations of the components may vary. However, the components do not need to be mixed into one cartridge.

(i) Biomaterial

In one embodiment, the biomaterial is a cell. The term "biomaterial" includes a composition (liquid, semi-solid, or solid) which contains cells, proteins, genes, peptides, or any combination thereof. In one embodiment, the biomaterial is viably maintained in a composition. In another embodiment, the biomaterial withstands the shear forces utilized in the methods described herein. Any cell is suitable for use as the biomaterial as determined by those skilled in the art. The composition may contain only one biomaterial or more than one biomaterial. In one embodiment, the cell is a mammalian cell, plant cell, bacterial cell, or viral capsid.

Examples of cells include, without limitation, cell solutions, cell aggregates, cell suspensions, cell-comprising gels, multicellular bodies, tissues, or any combination thereof. A number of cells may be selected and include differentiated and undifferentiated cells. In one embodiment the cells include, without limitation, contractile or muscle cells (e.g., skeletal muscle cells, cardiomyocytes, smooth muscle cells, and myoblasts), connective tissue cells (e.g., bone cells, cartilage cells, fibroblasts, and cells differentiating into bone forming cells, chondrocytes, or lymph tissues), bone marrow cells, endothelial cells, skin cells, epithelial cells, breast cells, vascular cells, blood cells, lymph cells, neural cells, Schwann cells, gastrointestinal cells, liver cells, pancreatic cells, lung cells, tracheal cells, corneal cells, genitourinary cells, kidney cells, reproductive cells, adipose cells, parenchymal cells, pericytes, mesothelial cells, stromal cells, undifferentiated cells (e.g., embryonic cells, stem cells, and progenitor cells), endoderm-derived cells, mesoderm-derived cells, ectoderm-derived cells, and any combination thereof.

A "stem cell" as used herein refers to mitotic cells which can differentiate into other cells. Stem cells may include, without limitation, totipotent cells, pluripotent cells, multipotent cells, oligopotent cells, and unipotent cells. Stem cells may include embryonic stem cells, peri-natal stem cells, adult stem cells, amniotic stem cells, and induced pluripotent stem cells.

Accordingly, the methods and systems described herein are useful in generating tissue, organs, and vascular tubes. "Tissue" as used herein refers to a grouping of mammalian cells of the same type that perform a specific function. Examples of tissues include, but are not limited to, connective (loose—areolar, reticular, and adipose and dense—regular and irregular), muscle (e.g., smooth, skeletal, and cardiac), nervous tissue (brain, spinal cord, and nerve), and epithelial (shape and arrangement classified), and special connective (cartilage, bone, blood). In one embodiment, intralumenal fluid perfusion may be used during the preparation of vascular tubes to mimic blood pressures.

An "organ" is a collection of mammalian tissues in a specific structure to perform a function. Examples of organs include, but are not limited to, skin, sweat glands, sebaceous glands, mammary glands, muscle, cartilage, bone marrow, bone, brain, hypothalamus, pituitary gland, pineal body, heart, blood vessels, cornea, heart valve, larynx, trachea, bronchus, lung, lymphatic vessel, salivary glands, mucous glands, esophagus, stomach, gallbladder, liver, pancreas, small intestine, large intestine, colon, urethra, kidney, adrenal gland, conduit, ureter, bladder, fallopian tube, uterus, ovaries, testes, prostate, thyroid, parathyroid, meibomian gland, parotid gland, tonsil, adenoid, thymus, and spleen, teeth, gums, hair follicle, trachea, cartilage, or any combination thereof.

A "vascular tube" as used herein refers to vessels or ducts that convey fluids such as blood, lymph, water, or any combination thereof to another location. The vascular tubes prepared as described herein have use in a variety of technologies including, without limitation, bypass grafting, arteriovenous access, drug testing, cardiovascular device testing, and as stents. In one embodiment, the vascular tube is selected from among arteries, elastic arteries, distributing arteries, arterioles, capillaries, venules, veins, large collecting vessels (such as the subclavian vein, the jugular vein, the renal vein and the iliac vein) and venae cavae. In a further embodiment, the vascular tube has a branched structure. In another embodiment, the vascular tubes prepared as described herein may be of a thickness to withstand pressures which are comparable to native physiological blood pressures. In a further embodiment, the vascular tubes may have an internal diameter of about 0.5 to about 6 mm.

The cell density necessary for the composition may and is dependent on the cells utilized and article fabricated using same. The cells may be pre-treated prior to incorporation into the composition using techniques such as incubation. The cell may also be at a selected temperature. In one embodiment, the cells are frozen, maintained at a lower temperature, at ambient temperature, or at above ambient temperature. In one embodiment, the cells are at about 37° C. or greater, depending on the type of cell. In a further embodiment, embodiment, bacterial cells are at about 37° C. or greater. In another embodiment, the cells are maintained at lower temperatures prior to, during or after printing.

(ii) Extrusion Agent

One or more extrusion agent may further be added to the composition described herein. In one embodiment, the extrusion agent cures, thereby encapsulating the biomaterial during formation of the fabricated article. The term "cure" or variations as used herein is utilized to describe the process for toughening or hardening one component of the composition described herein via the crosslinking of the components. In one embodiment, the curing occurs concurrently as the bioprinting proceeds (i.e., the curing and bioprinting occur simultaneously). The length of time required for the curing to complete depends on the components of the composition, article to be fabricated, and/or laboratory conditions, among others. In one embodiment, curing is complete in less than about 1 year. In another embodiment, curing is complete in about 1 second to about 1 year. In a further embodiment, curing is complete in about 1 second to about 1 minute.

The extrusion agent may cure in the absence of exogenous agents or techniques. In one embodiment, the extrusion agent is cured using electron beams, heat or chemical additives such as one or more photo-initiator as described below. In a further embodiment, the extrusion agent is curable at a wavelength of about 405 nm or greater.

In one embodiment, the extrusion agent is a support material. Two or more support materials, i.e., 2 to about 20, may be included in the composition. The support material is selected based on the desired quality, viscosity, permeability, elasticity or hardness, adherency, biocompatibility, 3D printed structure, or the like. The support material is capable of hardening, viscous, excludes cells from growing or migrating into or adhering to it, or any combinations thereof.

In one embodiment, the support material is curable or cross-linkable at a wavelength of about 405 nm or greater. The support material is optionally removed prior to use of the fabricated article. In one embodiment, the support material is removed via dissolution. Accordingly, the support material may be water-soluble, organic solvent soluble, dissolvable via enzymatic degradation, or dissolvable under acidic or basic conditions. In one embodiment, the enzymatic degradation is performed using a protease or lipase. The protease is, without limitation, proteinase K, protease XIV, α-chymotrypsin, collagenase, matrix metalloproteinase-1 (MMP-1), MMP-2, or any combination thereof. The dissolution may alternatively be performed using cations or ions.

A variety of support materials may be selected by one skilled in the art using the instant specification. In one embodiment, the support material is a polymer. In another embodiment, the support material is a thermoplastic polymer. In a further embodiment, the support material is polyethylene oxide, poly-caprolactone, poly(L)-lactic acid (PLLA), or gelatin methacrylate, or any combination thereof. In yet another embodiment, the polymer is, without limitation, diacrylates such as polyacrylic acid or polyethylene glycol diacrylate, methacrylates such as hydroxyethyl methacrylate, norborenes, hydrogel, NovoGel™, gelatin, Matrigel™, hyaluronan, poloxamer, peptide hydrogel, poly(isopropyl-n-polyacrylamide), polydimethylsiloxane, polyacrylamide, polylactic acid, silicon, silk, surfactant polyols, thermo-responsive polymers, hyaluronates, alginates, collagens, nanofibers, self-assembling nano fibers, hydrogels derived from collagen, hyaluronate, fibrin, agarose, chitosan, poly(ethylene oxide), polyvinyl alcohol, polyphosphazene, or derivatives, copolymers or any combination thereof. In yet a further embodiment, the diacrylate is PEG-DA. In still another embodiment, the methacrylate is PEG-MA. In a further embodiment, the norbornene is PEG-norbornene. In another embodiment, the polyoxyethylene is poly(ethylene glycol). One of skill in the art would be able to determine a suitable ratio of support material to cells depending on the other components of the composition.

(iii) Photo-Initiator

To create healthy 3D tissues, the damage to the cells by light (phototoxicity) must be minimized. Visible light reduces the energy that the tissues are exposed to. Thus, a photo-initiator also may be utilized in the composition described herein. In one embodiment, the photo-initiator promotes curing of the composition. In a further embodiment, the photo-initiator promotes cross-linking of one or more component of the composition. In another embodiment, the photo-initiator is a visible light photo-initiator. In a further embodiment, the photo-initiator is activated when exposed to blue light. In another embodiment, the photo-initiator is lithium phenyl-2,4,6-trimethylbenzoylphosphinate. In yet a further embodiment, the photo-initiator is the Irgacure™ 2959 product which contains one or more of the following:

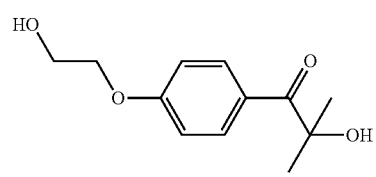

-continued

[Chemical structures shown]

The ratio of the polymer to the photo-initiator is dependent on the selection of the polymer for use as described herein. The amount of photo-initiator must be sufficient to initiate cross-linking of the polymer. In one embodiment, the weight ratio of the polymer to the photo-initiator is about 1:1 to about 20:1.

(iv) Optional Components

The composition may optionally contain additional agents to facilitate preparation of the desired product. One of skill in the art would readily be able to select suitable additional agents for use herein.

In one embodiment, the composition includes an extracellular matrix. Examples of extracellular matrix components include, without limitation, collagen, fibronectin, laminin, hyaluronates, elastin, proteoglycans, gelatin, fibrinogen, fibrin, or any combination thereof. The non-cellular components of the composition may be retained or may be removed prior to use using physical, chemical, or enzymatic means.

In a further embodiment, the composition includes a wetting agent as described above.

In yet a further aspect, the composition includes a cell-binding factor. Examples of cell-binding factors useful herein include, without limitation, fibronectin, lectins, cadherins, claudins, laminin, or any combination thereof.

In another embodiment, the composition includes an antioxidant. Examples of antioxidants include, without limitation, buffers such as phosphate buffered saline.

In a further embodiment, the composition includes an agent that inhibits cell death. Examples of agents that inhibit cell death include those that inhibit the activity of an interleukin, interferon, granulocyte colony-stimulating factor, macrophage inflammatory protein, transforming growth factor B, matrix metalloproteinase, capsase, MAPK/JNK signaling cascade, Src kinase, Janus kinase, or any combination thereof.

In yet another embodiment, the composition includes an agent that encourages cell adhesion. Examples of an agent that encourages cell adhesion include, without limitation, Arginine-Glycine-Aspartic Acid (RGD), integrin, and extracellular matrix (ECM).

In still a further embodiment, the composition includes polyoxypropylenes and polyoxyethylenes.

In another embodiment, magnetic fields may be used to guide cellular reorganization and migration of the various cell types. Accordingly, the compositions may contain magnetic particles such as ferromagnetic nanoparticles, and are subjected to magnetic fields to guide cellular reorganization and migration.

A viscosity agent may optionally be added to the composition. By doing so, maintenance or fidelity of the extruded layer may be achieved due to the imparted sufficient cohesive forces within the composition. In one embodiment the selected viscosity agent depends on the shear thickening or thinning of the components of the composition. In a further embodiment, the viscosity agent ensures that the composition is sufficiently viscous to maintain its shape when extruded. In another embodiment, the viscosity agent ensures that the composition is not too thick so as to prevent its extrusion. In one embodiment, the viscosity agent is poly(ethylene oxide), gelatin, Pluronic F-127 (i.e., a (polyethyleneoxide)-(polypropyleneoxide)-(polyethyleneoxide) based material), hyaluronic acid, or any combination thereof.

N. Fabricated Article

As discussed above, the methods, devices, and systems described herein permit the fabrication of a variety of articles using EMR at a wavelength of about 405 nm or greater. Accordingly, the fabricated article contains one EMR responsive material and cells as described above.

In one embodiment, the article is a cellular construct. In another embodiment, the article is 3-dimensional. In another embodiment, the article is a tissue construct such as an organ. In a further embodiment, the article is an array of cells. In still a further embodiment, the article is any body part (i.e., an organ) or organic structure to enhance and/or mediate bodily functions. In yet another embodiment, the article is a splint for implantation into a mammal, button (e.g., plug, stopgap, filling), among others.

The organ may be any component of a mammal. In one embodiment, the organ is skin, sweat glands, sebaceous glands, mammary glands, bone, brain, hypothalamus, pituitary gland, pineal body, heart, blood vessels, larynx, trachea, bronchus, lung, lymphatic vessel, salivary glands, mucous glands, esophagus, stomach, gallbladder, liver, pancreas, small intestine, large intestine, colon, urethra, kidney, adrenal gland, conduit, ureter, bladder, fallopian tube, uterus, ovaries, testes, prostate, thyroid, parathyroid, meibomian gland, parotid gland, tonsil, adenoid, thymus, spleen, teeth, gums, hair follicle, or cartilage.

A variety of plants or parts thereof may be printed using the methods and systems described herein. In one embodiment, the plant is algae, a plant which produces a natural product, an agricultural plant designed for human or animal ingestion, among others.

Bacteria and viral capsids may also be printed using the methods and systems described herein. In one embodiment, the bacterium is *Escherichia coli, streptococcus, Anaplasma, Basillus-brevis, Interrococcus*, among others. In another embodiment, the viral capsid is Adeno-associated, Aichi, Australian bat lyssa, BK polyoma, Banna, Barmah forest, Bunyamwera, Bunya La Crosse, Bunya snowshoe hare, caudiovirales, Cercopithecine herpes, Chandipura, Chikungunya, Cosa A, Cowpox, Coxsackie, Crimean-Congo hemorrhagic fever, Dengue, Dhori, Dugbe, Duvenhage, Eastern equine encephalitis, Ebola, Echo, Encephalomyocarditis, Epstein-Barr, European bat lyssa, GB C/Hepatitis G, Hantaan, Hendra, Hepatitis A, Hepatitis B, Hepatitis C, Hepatitis E, Hepatitis delta, Horsepox, Human adeno, Human astro, Human corona, Human cytomegalo, Human entero 68, 70, Human herpes 1, Human herpes 2, Human herpes 6, Human herpes 7, Human herpes 8, Human immunodeficiency, Human papilloma 1, Human papilloma 2, Human papilloma 16,18, Human parainfluenza, Human parvo B19, Human respiratory syncytial, Human rhino, Human SARS corona, Human spumaretro, Human T-lymphotropic, Human toro, Influenza A, Influenza B, Influenza C, Isfahan, JC polyoma, Japanese encephalitis, Junin arena, KI Polyoma, Kunjin, Lagos bat, Lake Victoria Marburg, Langat, Lassa, Lordsdale, Louping ill, Lymphocytic choriomeningitis, Machupo, Mayaro, MERS corona, Measles, Mengo encephalomyocarditis, Merkel cell polyoma, Mokola, Molluscum contagiosum, Monkeypox, Mumps, Murray valley encephalitis, New York, Nipah, Norwalk, O'nyong-nyong, Orf, Oropouche, Pichinde, Poli, Punta toro phlebo, Puumala, Rabies, Rift valley fever, Rosa A, Ross river, Rota A, Rota B, Rota C, Rubella, Sagiyama, Sali A, Sandfly fever sicilian, Sapporo, Semliki forest, Seoul, Simian foamy, Simian 5, Sindbis, Southampton, St. louis encephalitis, Tick-borne powassan, Torque teno, Toscana, Uukuniemi, Vaccinia, Varicella-zoster, Variola, Venezuelan equine encephalitis, Vesicular stomatitis, Western equine encephalitis, WU polyoma, West Nile, Yaba monkey tumor, Yaba-like disease, Yellow fever, or Zika, among others.

The fabricated article may have a single layer or multiple layers, depending on the desired use, and may be unicellular or multicellular. The fabricated article may also include repeating pattern of functional units. The functional unit may have any suitable geometry, including, circles, squares, rectangles, triangles, polygons, and irregular geometries. The repeating pattern of bioprinted functional units may be in the form of layers, i.e., a base layer and one or more layers thereon. The orientation of the layers is dependent on the final article to be fabricated. In one embodiment, the layers may all be in the same direction, may vary in direction, or any combination thereof. In another embodiment, the layers form a pattern. In a further embodiment, the layers are alternating. In still another embodiment, the layers lack any pattern. FIG. 14 provides an illustration of a tissue fabricated using the methods described herein. FIG. 14A depicts a three-dimensional cell patterning of a tissue-engineered construct. The three dimensional structure was composed of high strength synthetic polymer and a cell loaded hydrogel, fabricated by concurrent patterning of the two different materials. As shown in FIGS. 14B and 14C, two different materials, i.e., structural polymer 150 and cell loaded hydrogel 152, are concurrently deposited as a pattern to produce a single composite structure. FIG. 14B depicts a cross sectional view demonstrating the layer deposition. FIG. 14C depicts a top view demonstrating the lattice structure of the layered materials.

The fabricated article may be of any form which is useful to the attending clinician. In one embodiment, the fabricated article is a gel or solid.

The fabricated article may be formed by depositing a composition onto a receiving means. In one embodiment, the composition exits the orifice in the form of a droplet or stream. As described above, the composition cures after exposure to EMR of a wavelength of about 405 nm or greater.

Fabrication of the article may be continuous and/or substantially continuous. In one embodiment, fabrication of the article is continuous. In another embodiment, fabrication of the article is continuous with periods of inactivity. The fabricated article may be permitted sit for a sufficient time after formation, i.e., incubated. In one embodiment, the fabricated article sits so as to permit cell adhesion, reorganization migration, or any combination thereof. Additional methods for facilitating incubation may be performed utilized and include, without limitation, heating, cooling, pressure, tension, compression, mechanical forces, humidity changes, or any combination thereof.

At the end of the incubation period, the cells may be isolated by removing any non-essential components. In one embodiment, any unwanted components such as the support medium and/or extrusion agent is removed. In another embodiment, the support medium is physically removed away from the support medium. In another embodiment, the support medium is removed using water or any solvent that the non-cellular material is soluble in.

Finally, the fabricated article, lacking any non-essential components, may be finalized by permitting the cells to mature. In one embodiment, the fabricated article is place in a maturation chamber for growth.

O. Kits

Also provided are kits or packages containing any component of the bioprinter described herein. In one embodiment, the kit or package contains one or more of a printer stage, receiving means, cartridge, dispensing means such as a syringe, capillary tube, or pipette, air compressor, EMR source, software, non-transitory computer readable storage medium, computer module, graphic user interface, optical device, among others, or any combination thereof.

The kit or package may also include one or more component of the composition. In one embodiment, the kit or package contains one or more biomaterial such as cells. In another embodiment, the kit or package contains one or more of an extrusion agent, photo-initiator, extracellular matrix, antioxidant, agent that inhibits cell death, agent that encourages cell adhesion, magnetic particles, viscosity agent, extrusion agent such as support material, among others, or any combination thereof.

The kit or package may further include one or more of a vial, tube, applicator, needle, dispensing means, lid, sealant, foil, and other appropriate packaging and instructions for use.

The kit may contain one or more component of the composition. One or more component of the composition may be separate, two or more components may be combined, or any combination thereof. In one embodiment, all of the components of the composition may be combined in a single dispensing means in the kit. In another embodiment, each component of the composition may be contained in a separate dispensing means in the kit. In a further embodiment, some of the components are individually present in a dispensing means and some of the components are combined in a single dispensing means.

P. Methods of Using the Bioprinters

The bioprinters described herein and the fabricated synthetic, i.e., man-made articles produced thereby have a variety of uses. In one embodiment, the fabricated articles in the form of organs may be transplanted into a mammal in need thereof. The organs may be transplanted in the absence or presence of immunosuppressant agents as determined by the attending physician and transplanted organ. In one embodiment, immunosuppressant agent may be administered, prior to, concurrently with, or subsequent to the transplantation. In another embodiment, the anti-rejection agent is an induction, maintenance, immunosuppressant. In a further embodiment, the anti-rejection agent is, without limitation, atgam, azathioprine, basiliximab, cyclosporine, daclizumab, methylprednisolone, mofetil, muromonab-CD3, mycophenolic acid, mycophenolate mofetil, OKT3, prednisone, rapamycin, sirolimus, tacrolimus, thymoglobulin, or any combination thereof. Additional agents may be administered prior to, concurrently with, and subsequent to the transplantation and include, without limitation, pain medications, among others.

The fabricated synthetic articles produced as described herein also have use in testing a wide variety of chemical agents. By doing so, the necessity to perform animal testing may be reduced or eliminated. Specifically, functions inherent to the particular cells of the fabricated articles may be evaluated, i.e., ensuring that the cells are properly functioning. Such functions include, without limitation, protein function, cell marker viability, cell adhesion, or cell contraction. Accordingly, the sensitivity, viability, toxicity, and resistance, among others, of the chemical agents may be evaluated. Accordingly, the fabricated synthetic articles produced herein have use in vitro tests across a number of industries. The term "chemical agent" as used herein refers to any single chemical or composition containing that chemical agent which must be tested prior to distribution to the public. In one embodiment, the chemical agent may be household chemicals, pharmaceuticals such as antibiotics and chemotherapeutic agents, environmental agents, agricultural chemicals, food additives, healthcare agents, among others. In doing so, the chemical agent may be applied to a cellular structure prepared using the bioprinters herein. After application, the cellular structure may be monitored. In one embodiment, the viability of the cells in the cellular structure may be monitored and measured as necessary.

Q. Embodiments of the Invention

Figure 15:
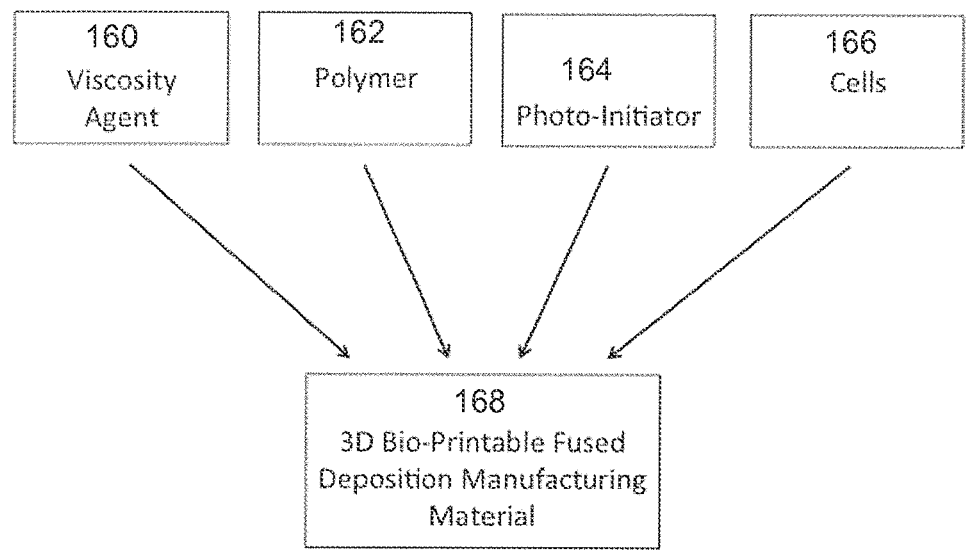
FIG. 15 is a diagram illustrating embodiments of compounds utilized to prepare the compositions described herein.

FIG. 15 illustrates one embodiment of a composition which utilizes viscosity agent 160, polymer 162, blue light photo-initiator 164, and cells 166 to provide tissue 168.

FIG. 16 depicts various possibilities of compositions for use in multiple cartridges. If using a single cartridge, viscosity agent 160, polymer 162, photo-initiator 164, and cells 166 are mixed into single syringe 170. If using two cartridges, viscosity agent 160 is deposited separately from the other ingredients, i.e., polymer 162, photo-initiator 164, and cells 166 using syringe 172. The contents of syringe 170 can be used in parallel across several cartridges.

R. Examples

Example 1: Cell-Based Bowl

Figure 17:
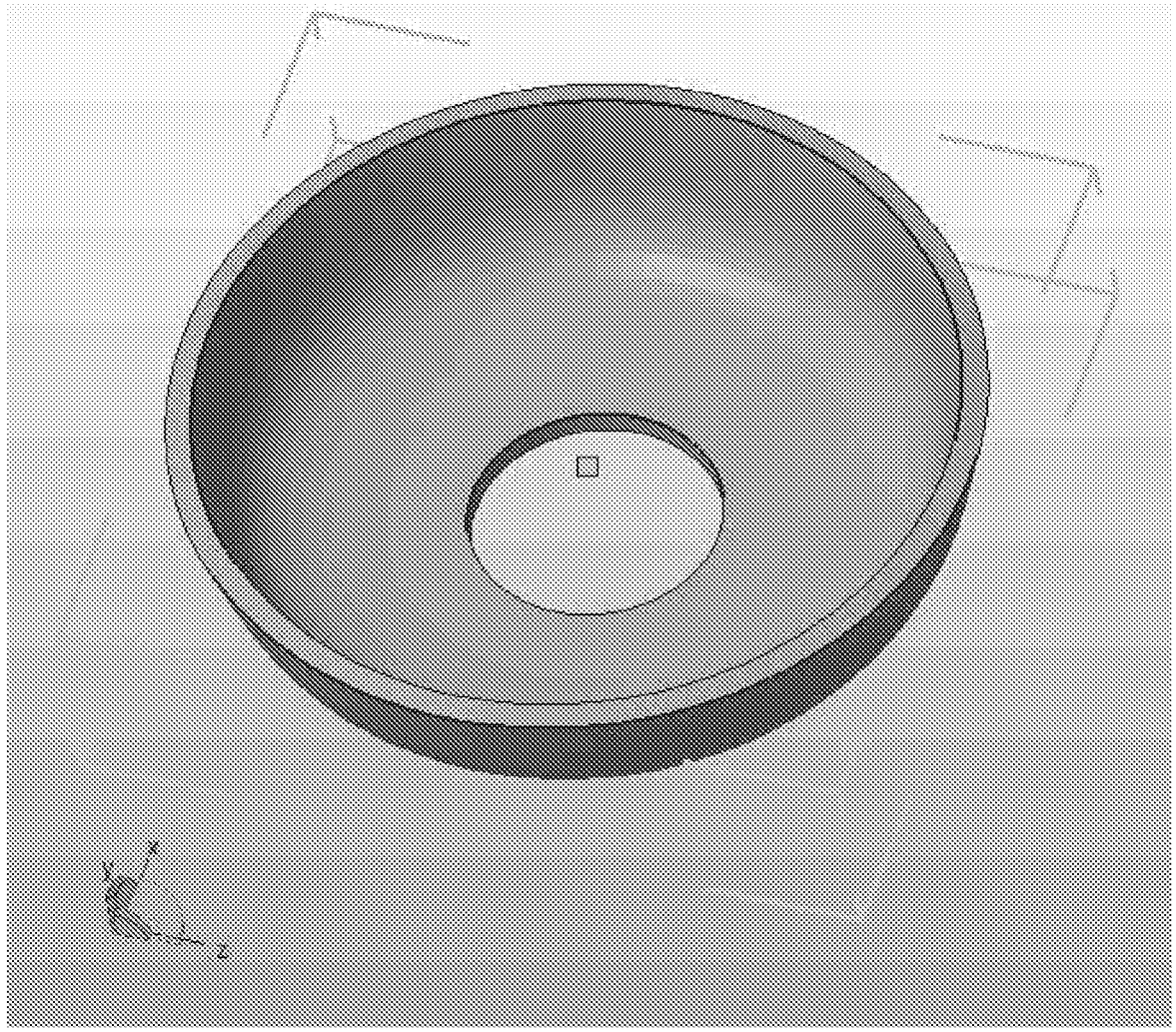
FIG. 17 is a bowl construct designed on the 3D CAD Solidworks® software.

A cell-based construct was designed on the 3D CAD Solidworks™ software as a bowl material and exported as a standard tellellation language (stl) file. See, FIG. 17.

A polyethyelene glycol (PEG) based material (1000 MW) is combined with deionized water at a 20% weight per volume ratio to form a solution. Polyethylene oxide at a 5.5% ratio with the PEG and lithium phenyl-2,4,6-trimethylbenzoylphosphinate mixed at a 0.5% ratio with the PEG were then added to the polyethylene glycol solution. Human mesenchymal stem cells were then pipetted into the combined solution and the solution mixed for 1-2 minutes. The final mixture was then added to a syringe and placed within a cartridge of a bioprinter described above. The composition was extruded at a pressure of 275 kPa (40 psi) to prepare a bowl.

Figure 18:
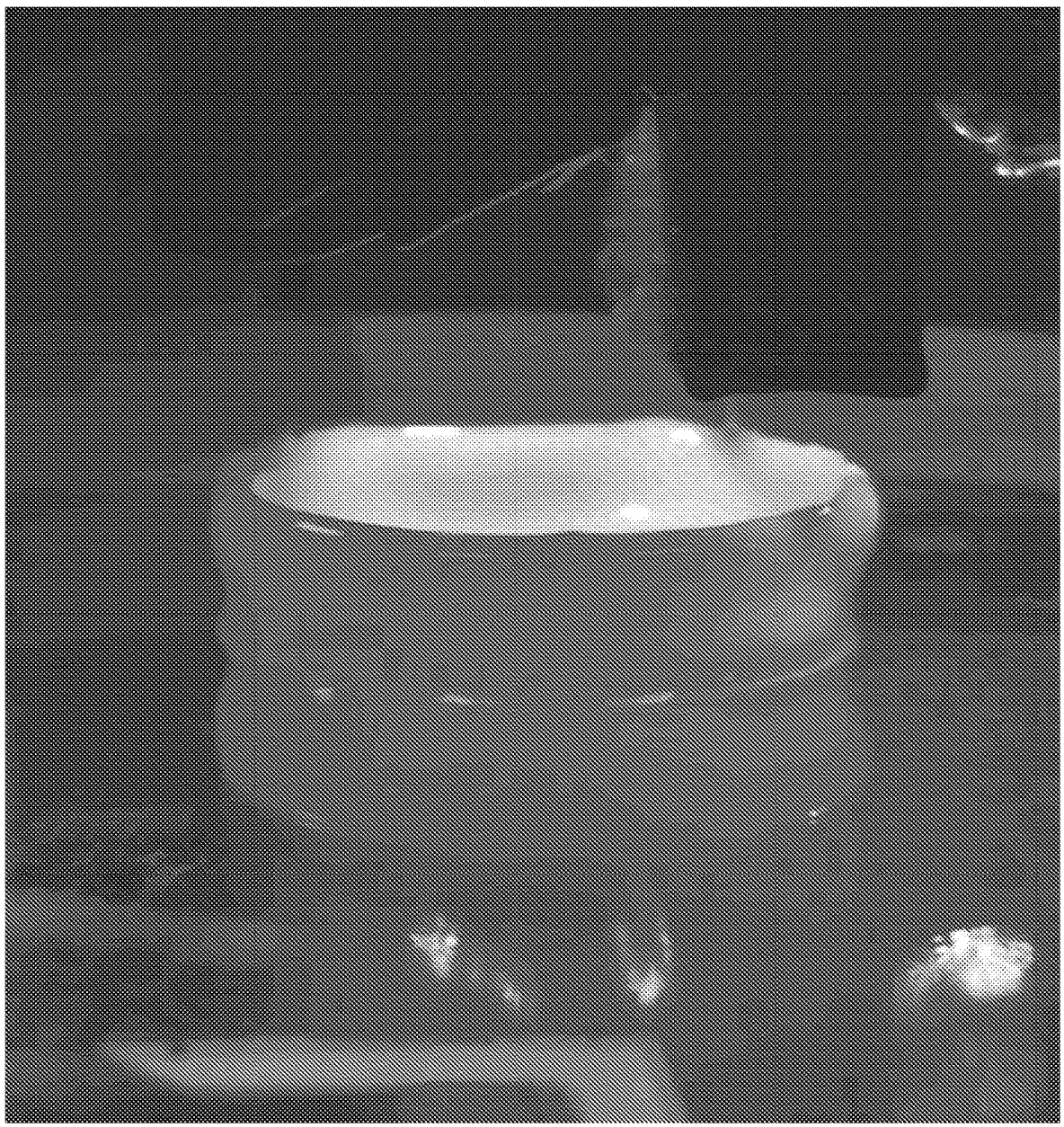
FIG. 18 is a photograph of a cell-based bowl prepared using the methods and systems described herein.

After printing, the bowl was incubated for 8 hours under cell culture media at 37° C. A cell viability assay was conducted using a live/dead kit assay from LifeTechnologies and illustrated that about 90% of the cells were alive. See, FIG. 18.

Example 2: Synthetic Ear

Figure 19:
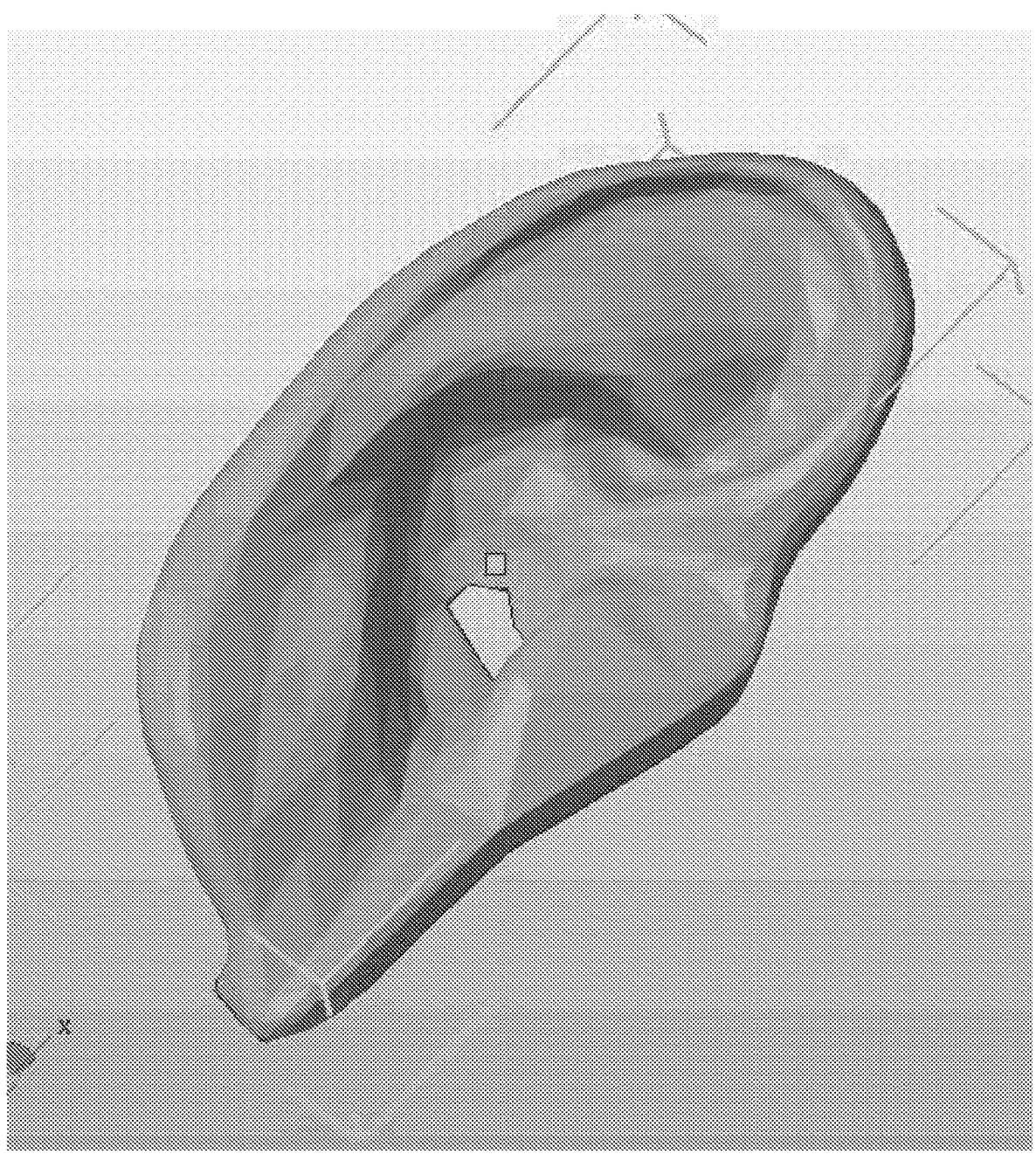
FIG. 19 is an ear construct designed on the 3D CAD Solidworks® software.

A cell-based construct was designed on the 3D CAD Solidworks™ software as an ear and exported as an stl file. See, FIG. 19.

A polyethyelene glycol based material (1000 MW) is combined with deionized water at a 20% weight per volume ratio to form a solution. Polyethylene oxide at a 5.5% ratio with the PEG and lithium phenyl-2,4,6-trimethylbenzoylphosphinate mixed at a 0.5% ratio with the PEG were then added to the polyethylene glycol solution. Human mesenchymal stem cells were then pipetted into the combined solution and the solution mixed for 1-2 minutes. The final mixture was then added to a syringe and placed within a cartridge of a bioprinter described above. The composition was extruded at a pressure of 275 kPa (40 psi) to prepare an ear.

Figure 20:
FIG. 20 is a photograph of a synthetic ear prepared using the methods and systems described herein.

After printing, the ear was incubated for 8 hours under cell culture media at 37° C. A cell viability assay was conducted using a live/dead kit assay from LifeTechnologies and illustrated that about 90% of the cells were alive. See, FIG. 20.

When ranges are used herein, all combinations, and subcombinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A three-dimensional bioprinter comprising:
 a material deposition device comprising:
  a cartridge for receiving and holding a composition comprising biomaterial that cures after exposure to electromagnetic radiation (EMR) at or above 405 nm, and
  an extruder configured to engage with the cartridge and extrude the composition;
 a receiving plate positioned below the cartridge configured to receive the composition; and
 an EMR module configured to emit EMR at a wavelength of about 405 nm or higher, wherein the EMR module is integrated with the cartridge and configured to emit EMR towards at least one of the receiving plate and the cartridge.

2. The bioprinter of claim 1, wherein the material deposition device is configured to extrude simultaneously as the EMR module emits the EMR.

3. The bioprinter of claim 1, wherein the EMR module is configured to emit EMR for about 1 to about 5 seconds.

4. The bioprinter of claim 1, wherein the extruder comprises a syringe, capillary tube, or micropipette.

5. The bioprinter of claim 1, wherein said bioprinter comprises a first opening which permits insertion of said cartridge and a second opening which permits a portion of said cartridge to exit said bioprinter.

6. The bioprinter of claim 5, wherein said first opening is about 1 μm to about 10 cm and said second opening is about 1 μm to about 10 cm.

7. The bioprinter of claim 5, wherein said cartridge has a capacity of about 1 μL to about 100 mL and diameter of about 1 μm to about 10 cm.

8. The bioprinter of claim 1, wherein said cartridge houses dispensing means contains comprising a needle having a luminal diameter of about 10μ to about 5 cm.

9. The bioprinter of claim 5, further comprising adhesive foil over said second opening.

10. The bioprinter of claim 1, wherein said EMR module is adjacent to or houses said cartridge.

11. The bioprinter of claim 1, wherein said EMR module comprises an attenuation filter which lowers or raises the intensity of the EMR emittance.

12. The bioprinter of claim 1, further comprising a printer stage.

13. The bioprinter of claim 1, further comprising a temperature means for adjusting the temperature of said bioprinter to about −10 to about 300° C.

14. The bioprinter of claim 1, wherein said composition is dispensed using pressure or electrical current, wherein said pressure is generated using a piston, compressed gas, hydraulics, or any combination thereof.

15. The bioprinter of claim 1, wherein said EMR module exposes said composition to EMR of a wavelength of about 405 nm or greater prior to, during, or after dispersion.

16. The bioprinter of claim 1, comprising two or more cartridges.

17. The bioprinter of claim 1, wherein said receiving plate is leveled to 0° relative to the flat bottom of said cartridge.

18. The bioprinter of claim 1, further comprising a computer module including at least one of a processor and a non-transitory computer readable storage media encoded with computer readable program code configured to operate the bioprinter.

19. The bioprinter of claim 1, wherein said biomaterial comprises cells.

20. The bioprinter of claim 1, wherein said composition further comprises an extrusion agent which is curable at a wavelength of about 405 nm or greater, a photo-initiator, viscosity agent, or biocompatible agent.

21. The bioprinter of claim 20, wherein said extrusion agent is a polyoxyalkylene, diacrylate, methacrylate, norbornene, gelatin, methacrylate, methacrylated hyaluronic acid, hydroxyethyl-methacrylate-derivatized-dextran, p(HP-MAm-lactate)-PEG, gold nanorods, carbon nanotubes, collagen, polyethylene oxide, poly-caprolactone, poly(L)-lactic acid, or any combination thereof.

22. The bioprinter of claim 20, wherein said photo-initiator is lithium phenyl-2,4,6-trimethylbenzoylphosphinate or one or more of the following:

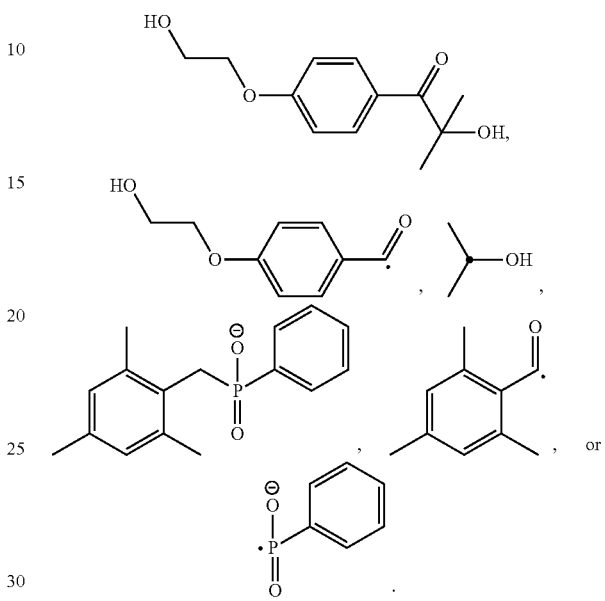

23. The bioprinter of claim 20, wherein said viscosity agent is poly(ethylene oxide), gelatin, Pluronic F-127, hyaluronic acid, or any combination thereof.

24. The bioprinter of claim 1, wherein said composition further comprises a wetting agent, antioxidant, agent that inhibits cell death, an agent that encourages cell adhesion, cell-binding factors, or any combination thereof.

25. The bioprinter of claim 24, wherein said cell-binding factor is fibronectin, a lectin, a cadherin, a claudin, laminin, or any combination thereof.

26. The bioprinter of claim 1, wherein said composition is dispensed with an accuracy of about ±50 p.m on one or more axis.

* * * * *